United States Patent [19]

Freeman, Jr. et al.

[11] Patent Number: 6,012,035
[45] Date of Patent: Jan. 4, 2000

[54] SYSTEM AND METHOD FOR SUPPORTING DELIVERY OF HEALTH CARE

[75] Inventors: Berkley Irving Freeman, Jr., Berthoud; Edgar William Smith, Boulder, both of Colo.

[73] Assignee: Integral Business Services, Inc., Denver, Colo.

[21] Appl. No.: 08/951,818

[22] Filed: Oct. 13, 1997

Related U.S. Application Data

[63] Continuation of application No. 08/423,523, Apr. 17, 1995, abandoned, which is a continuation-in-part of application No. 08/088,932, Jul. 8, 1993, abandoned.

[51] Int. Cl.$^7$ .................................................. G06F 17/60
[52] U.S. Cl. ........................ 705/2; 235/379; 235/380; 705/40; 705/41; 705/44
[58] Field of Search .................. 705/3, 2, 4, 1, 705/7, 39, 40, 41–44; 235/379, 380, 376

[56] References Cited

U.S. PATENT DOCUMENTS

| | | | |
|---|---|---|---|
| 4,237,344 | 12/1980 | Moore | 379/38 |
| 4,315,309 | 2/1982 | Coli | 705/3 |
| 4,346,442 | 8/1982 | Musmanno | 705/36 |
| 4,491,725 | 1/1985 | Pritchard | 705/2 |
| 4,857,716 | 8/1989 | Gombrich et al. | 235/375 |
| 4,858,121 | 8/1989 | Barber et al. | 364/406 |
| 4,916,611 | 4/1990 | Doyle, Jr. et al. | 705/2 |
| 5,065,315 | 11/1991 | Garcia | 705/2 |
| 5,070,452 | 12/1991 | Doyle, Jr. et al. | 705/2 |
| 5,179,569 | 1/1993 | Sawyer | 375/202 |
| 5,193,056 | 3/1993 | Boes . | |
| 5,193,057 | 3/1993 | Boes | 705/31 |
| 5,220,501 | 6/1993 | Lawlor et al. | 364/408 |
| 5,235,507 | 8/1993 | Sackler et al. | 705/2 |
| 5,291,399 | 3/1994 | Chaco | 364/413.02 |
| 5,301,105 | 4/1994 | Cummings, Jr. | 705/2 |
| 5,301,262 | 4/1994 | Ertel | 364/413.01 |
| 5,542,420 | 8/1996 | Goldman et al. | 128/630 |
| 5,544,044 | 8/1996 | Leatherman | 395/203 |
| 5,550,734 | 8/1996 | Tarter et al. | 395/202 |

OTHER PUBLICATIONS

"Financial Data Organizations Seek Piece of Health Care Pie", Electronic Claims Processing Report., Feb. 21, 1994, v. 2, No. 4, Published by Phillips Business Info.

"The EDI Coalition Buys Translation Software From Med–Link Technologies" Automated Medical Payment News (Faulkner & Gray, Inc., publisher) vol. 3, No. 7, Jul. 6, 1994.

*Primary Examiner*—Joseph Thomas
*Attorney, Agent, or Firm*—E. C. Hancock; F. A. Sirr; Holland & Hart LLP

[57] ABSTRACT

Effectuation of a health care provision agency cooperative function is established through a communication network linking all the various entities of the cooperative. The entities include the third party payor members, the health providing individuals, clinics, or the like, along with secondary providers including pharmacies and laboratories, health care facilities such as hospitals, and the several entities associated with management of the cooperative and appropriate funds transfer functions. A coordinating interface system maintains data storage of the necessary information, and manages the entity intercommunications in accordance with the basic structure of the active and eligible elements of the agency cooperative.

4 Claims, 3 Drawing Sheets

SYSTEM AND METHOD FOR SUPPORTING DELIVERY OF HEALTH CARE

This application is a continuation of Ser. No. 08/423,523, filed Apr. 17, 1995, now abandoned which is a continuation-in-part of U.S. patent application Ser. No. 08/088,932 filed Jul. 8, 1993, now abandoned, for SYSTEM AND METHOD FOR SUPPORTING DELIVERY OF HEALTH CARE by B. I. Freeman, Jr. and E. W. Smith.

BACKGROUND OF THE INVENTION

1. Field of the Invention

The present invention relates to systems and processes for supporting the delivery of health care to individuals. More particularly, the present invention relates to devices and methods dedicated to effectuating the provision and management of a cooperative health care system in connection with an integrated cooperative group of entities. The present invention is concerned with a new paradigm of systems concerned with, and supported by, communications and computer networks and methods of using the same for providing medically oriented services while coordinating the various functions associated therewith.

2. Description of the Related Art

Historically, the dispensation of health care has generally occurred in a fragmented manner. Typically, individuals obtain medical services from health care providers; i.e., physicians, pharmacies, hospitals, or the like as needed. Increasingly over the past sixty years, these services have received coverage by some form of third party payor, such as the employer, the government, or an insurance mechanism, with the balance payment remaining the responsibility of the patient. Sometimes the patient pays directly for the services, and sometimes payment is effected by use of credit through a credit card company or the like. At other times, claims are submitted by the patient or by the provider to an insurance company who then pays the provider, patient, or both, as appropriate. There are many inefficiencies and inequalities inherent in this disjointed health care system and procedure.

Some business organizations have sprung up as health maintenance organizations which have prearranged service availability with particular health care providers where access, availability and methodology of treatment modalities are directly related to the structure and the payment mechanism inherent in vertically oriented organizations and related systems. Such arrangements tend to restrict the ability of the patient to select someone better known, or more desirable as a particular health care provider, to handle the particular problem.

Some prior art medical applications have employed computer systems and communications networks for various purposes. For example, U.S. Pat. No. 5,065,315 by Garcia employs a computer-based system for collecting patient data and producing time oriented task lists within a given hospital facility. In U.S. Pat. No. 4,491,725 by Pritchard, medical insurance coverage verification is initiated from a patient identifying card so as to access a central database through a data processing network.

Still other data processing systems have utilized computer programs, computers and data processing communication networks to interconnect a plurality of care providers, banks and insurance companies through a central computer to allow determinations of coverage and payments for patients, such as in U.S. Pat. No. 4,858,121 by Barber et al, U.S. Pat. No. 4,916,611 by Doyle et al, and U.S. Pat. No. 5,070,452 by Doyle et al. Such prior art arrangements have not provided the systems and methods for effectuating a fully integrated and cooperative system for dispensing and managing health care.

SUMMARY OF THE INVENTION

The functions associated with health care provision assistance, in accordance with the present invention, advantageously utilize communicating computer equipment and a multiplicity of interconnected terminals and locations all associated with one or more of the multiple facets of an agency-cooperative health care provision and management system. Health care providers (such as doctors, hospitals, pharmacies and the like), insurance companies (including employer self insurance programs, no fault insurance programs, and government programs) and a financial institution are connected via computer terminal to a central data switch and repository computer which provides the interface between the terminals and records every transaction among the terminals. The data switch and repository is also connected to terminals associated with a coordinated management system. The management system handles the system housekeeping functions of the cooperative by monitoring the databases within the repository to ensure adequate performance by service providers and insurance companies.

A qualified member is issued an electronic card, or the like, by the financial institution, which also provides a credit level to the member. When the member visits a health care provider, the provider sends a diagnostic code to the member's insurance company and requests an authorization code which indicates the eligibility of the member for health care. The financial institution indicates whether the member has credit. After the member has received medical treatment, the provider submits a claim to the insurance company, which adjudicates the claim and notifies the financial institution to pay the claim on behalf of the third party payor and the insured member. The financial institution pays the provider's claim in full, minus a transactional fee used to pay for the bank's services and a reserve account to cover bad debt and charity care. The insurance company, or third party payor, sends an explanation of benefits to the provider, and also to the member showing which portion of the claim was paid by the insurance company and which must be paid by the patient. The bank bills the patient for the patient's share of the provider's bill which the bank has advanced. The patient and insurance company bills include a service charge to pay for the data switch and repository and management services. The bank also sends a detailed financial transaction report to the provider.

All of the transactions among the provider, insurance company, and financial institution are interfaced through the data switch and repository which records each transaction. The data switch and repository could consist of all of the databases located at the various entities. However, for redundancy and backup, in the preferred embodiment, the data switch and repository is a separate database which downloads and records all of the transactions between the entities of the system. Thus, the repository can provide statistical reports to the providers, insurance companies, and management service which are useful in assessing such matters as treatment effectiveness, insurance company performance, profitability, and conformance with cooperative group requirements.

Thus, the initiation of a medical care request by the subscriber member sets in motion a chain of events evolving around the various facets of the horizontally integrated agency cooperative. The functions involve verification of the insurance eligibility and credit of the member, membership status of the health care provider, and electronic transfer of accounting related data, including electronic claim processing and the transfer of funds by the financial institution (on behalf of third party payors and insured members).

The system and method of this invention is directed to the purpose of effectuating the operation of a cooperative agency organization dedicated to health care provision and management amongst a plurality of groups of entities. These entities include health care providers, health care facilities, a financial institution and third party payor members each of which has one or more health care users as constituents. A data switch and repository interfaces among these entities and the management service and stores records of all transactions between the entities.

A plurality of terminals are assigned to respective entities of the cooperative agency organization, and a data switch and repository interfaces among the entities' terminals for determining that a user is eligible for health care and for authorizing funds transfers correlated to services provided by a cooperative health provider to an authorized user. A particularly attractive device for facilitating determination of eligibility is the contemporary electronic cards each assigned to a respective one of the members for enabling automatic communication with the information storage. Such a card acts as a national bank credit card for health care for the insured member, as an I.D. card for the insurance company, as an access card to the system, and as a vehicle for health care providers to submit claims and get paid.

The data switch and repository can provide for interconnections amongst the health care providers and the health care facilities for permitting communications therebetween directed to health care provision to the member based upon establishment of eligibility of the member through an earlier inquiry of a provider or facility.

The method of this invention likewise effectuates the monitoring and management of a cooperative health care provision system through a management service. As mentioned, these entities typically include health care providers, health care facilities, a financial institution, and third party payors or subscribers who have one or more health care users as members. The method includes the initial and subsequent steps of providing interfacing between the entities, storing records of a transactions between entities, and providing statistical reports based on the transactions.

A request for information from a provider causes a response by determining that the provider is included in the listing of active members. A provider favorably thus determined in accordance with the responding step is allowed to have access to the database for determining that a user is eligible for health care and has credit. Thereafter, funds transfers are authorized in correlation to services provided by a cooperative health provider to an authorized user.

The system administrative time is reducible by the step of enabling the health care providers and health care facilities to cooperatively provide health care service to a user after a favorable determining response has resulted from the original provider inquiry.

Those having normal skill in the art will recognize the foregoing and other objects, features, advantages and applications of the present invention from the following more detailed description of the preferred embodiments as illustrated in the accompanying drawings.

DETAILED DESCRIPTION OF THE PREFERRED EMBODIMENT

Figure 1:
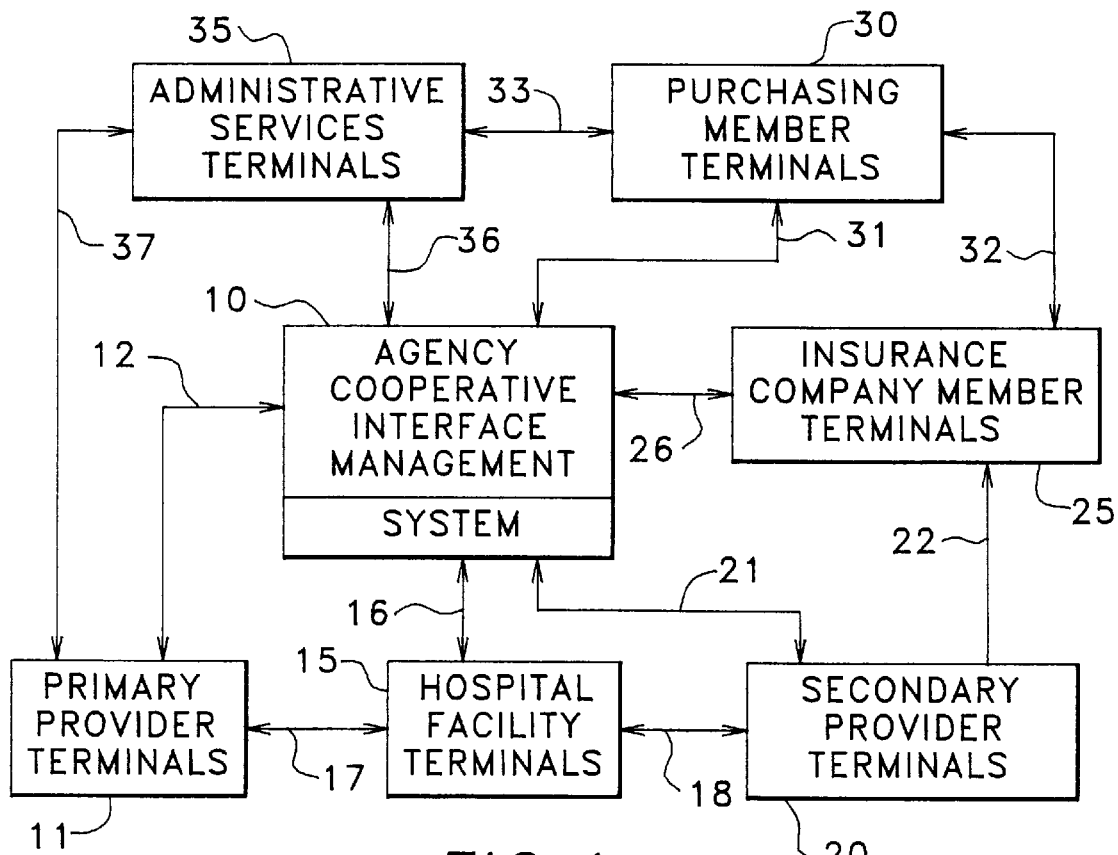
FIG. 1 is a system block diagram illustrating communication between entities in accordance with the present invention.

FIG. 1 shows the interactions and communication between entities which cooperate as a collaborative health care system according to the present invention. The agency cooperative interface management system 10 is shown at the center of the diagram because management system 10 monitors and manages the system. Other elements of the system include administrative services terminals 35, purchasing members terminals 30, insurance company member terminals 25, secondary provider terminals 20, hospital facility terminals 15, and primary provider terminals. Communications occur between and among the entities' terminals through communications lines 12, 16, 17, 18, 21, 22, 26, 31, 32, 33, 36, and 37.

More particularly, FIG. 1 presents a general block diagram of the system configuration for a typical data processing network to effectuate the cooperative functions involved in the various entities for a fully integrated medical delivery and accounting system. The entities here involved cooperate as a collaborative health care system which offers more efficient delivery of medical care products and services at consequently lower costs, while establishing a vehicle by which all of the participating members in the system can have a voice in fashioning a series of cooperative interrelationships that work to the benefit of each facet of the cooperative.

The system intended for support by the FIG. 1 network is essentially a cooperative of buyers and sellers of products and services used in, or useful to, the health care industry. Such a system might have five or more voting segments with the entities of each segment generally related by similarity of business or professional interest so that no particular vested interest can control the decision making by the cooperative.

The interface management system 10 coordinates the vital functions of the cooperative. It obtains listings of the health provision entities, such as the primary health care providers 11 who have appropriate terminals to allow communication via communication links 12 with the coordinating management terminals 10. The terminals 11 are presumed assigned to the various physicians or other licensed health care facilities, such as clinics. An important segment of the cooperative are the hospitals and other licensed health care facilities which have agreed to become part of the cooperative and thus were assigned terminals 15 for communicating with the primary providers 11 over links 17 and with the coordinating interface 10 over links 16.

Secondary health care providers, such as laboratories, pharmacies, medical products suppliers and manufacturers, and the like, are assigned terminals 20 for communicating with the coordinating terminals 10 over links 21, and with insurance business entities at their terminals 25 which, in turn, communicate with the coordinator over links 26. The subscribers or purchasing members of the cooperative are employers, their employees, individuals, groups of individuals, associations, trusts, agents and the like. These are assigned terminals 30 for communicating with the other components of the cooperative as shown. It is the individuals, employees and members of the various organizations who are associated with these purchasing entity terminals 30 who essentially drive the interactions of the components of the system.

For purposes of the present example, the final cooperative group segment is assigned the administrative services terminals 35. The functions here provided are the general administration, legal services, accounting services, banking functions, financial organizations (such as credit companies), claims processors, data processing functions, and the like. Their terminals are coupled with the other system functions via links 33, 36 and 37.

Note that the outer loop, including communication links 17, 18, 22, 32, 33 and 37, is intended to indicate that any of the outer terminals on this loop can communicate with one or more terminals likewise on that loop, in addition to communicating with the centralized interface management system 10. Thus, a physician with a primary provider terminal 11 can communicate directly with the terminal 25 of an insurance entity to directly enter a claim upon providing services to an eligible (or at least prospectively eligible) subscriber. In addition, that same physician at a terminal 11 can contact a secondary provider terminal 20, such as for having a prescription filled.

The overall cooperative can readily eliminate duplication of services by the mutual agreement of the various components through the coordinating efforts of the interface management system 10.

In operation, the cooperative members are provided with an authorizing entry in a database managed and compiled by the interface system 10 when an appropriate service and fee payment is established by a member user associated with a terminal 30. The individuals are then given an identification code which preferably would take the form of an electronic access card or bank card. This allows access to the substantial technical capacity of member financial and banking services. This feature, including identification, billing and payment mechanisms, represents a potential savings over the administration of contemporary health provision systems.

The overall cooperative is based upon a membership which mutually agrees to the agency cooperative business relationship with potentially democratic management thereof. Thus, a network of interdependent agreements make up the cooperative thereby realizing increased efficiencies and economies of scale while lowering the costs to the members and subscribers. As a result, a managed and collaborative health care marketplace is created that ensures the availability and quality of care in a given locale or region. The cooperative structure can accommodate a single payor, or any third party arrangement, even to the extent of an entire Medicaid or Medicare system as a purchasing member. The arrangement promotes the provision of competitive quality health care services and the collective well being of the cooperative members.

A purchaser database is built and maintained as the responsibility of the agency management 10 and it is administered for the cooperative management system. The agency builds a database of the various members of the cooperative, including listings of providers, facilities, administrators including finance related entities, insurance entities and purchasing members. Whenever a purchasing member has entered the cooperative, the agency management 10 collects enrollment data of the actual health care users from that purchasing member of the cooperative.

The collected data is then transferred to an administrator terminal 35 who creates a database entry. The administrator transfers the enrollment data to a bank such as at another terminal 35, and/or to an insurance terminal 25. The administrator archives the data set as a backup, since the user-accessed database is now available to the bank and/or insurance member.

Periodically, changes in the enrollment data will occur as with employees hired by, or leaving, an employer purchasing member. The subscriber, or purchasing member, at their terminal 30 notifies the coordinating agency of these changes. The data management thereafter is similar to that described above for new enrollment data.

Figure 2:
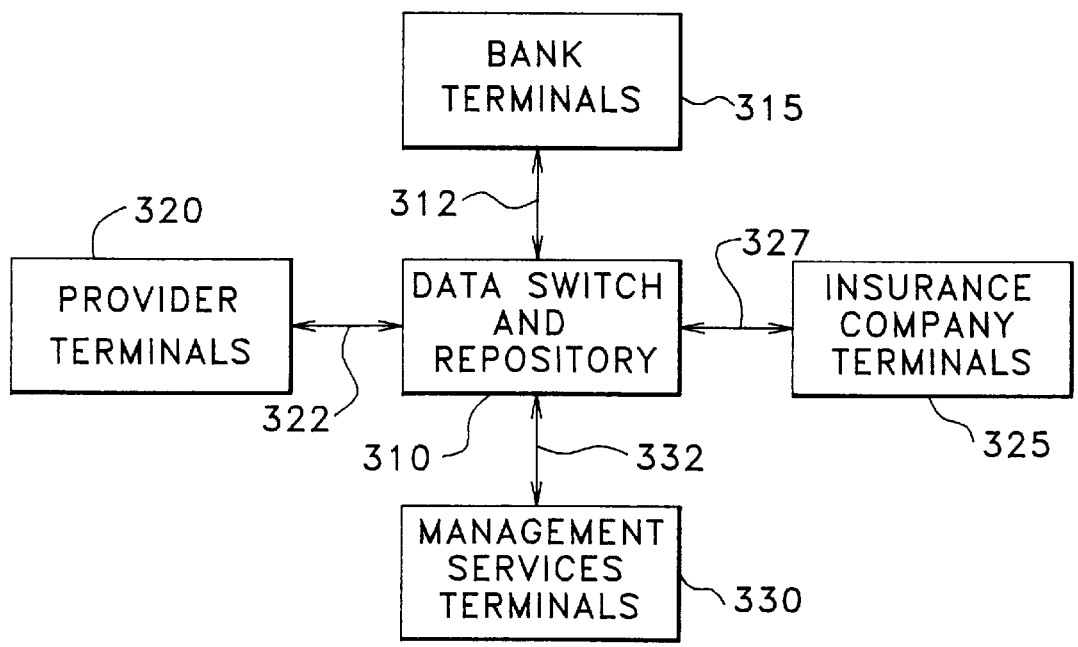
FIG. 2 is a system block diagram illustrating the apparatus which establishes the interrelationships between the various entities' terminals in accordance with the present invention.

FIG. 2 presents a general block diagram of the system configuration for a typical data processing network to effectuate the cooperative functions involved in the various entities shown in FIG. 1 for a fully integrated medical delivery and accounting system. The entities here involved cooperate as a collaborative health care system which offers more efficient delivery of medical care products and services at consequently lower costs, while establishing a vehicle by which all of the participating members in the system can have a voice in fashioning a series of cooperative interrelationships that work to the benefit of each facet of the cooperative.

The system intended for support by the FIG. 2 network is essentially a cooperative of buyers and sellers of products and services used in, or useful to, the health care industry. Such a system might have five or more voting segments with the entities of each segment generally related by similarity of business or professional interest so that no particular vested interest can control the decision making by the cooperative.

Figure 4:
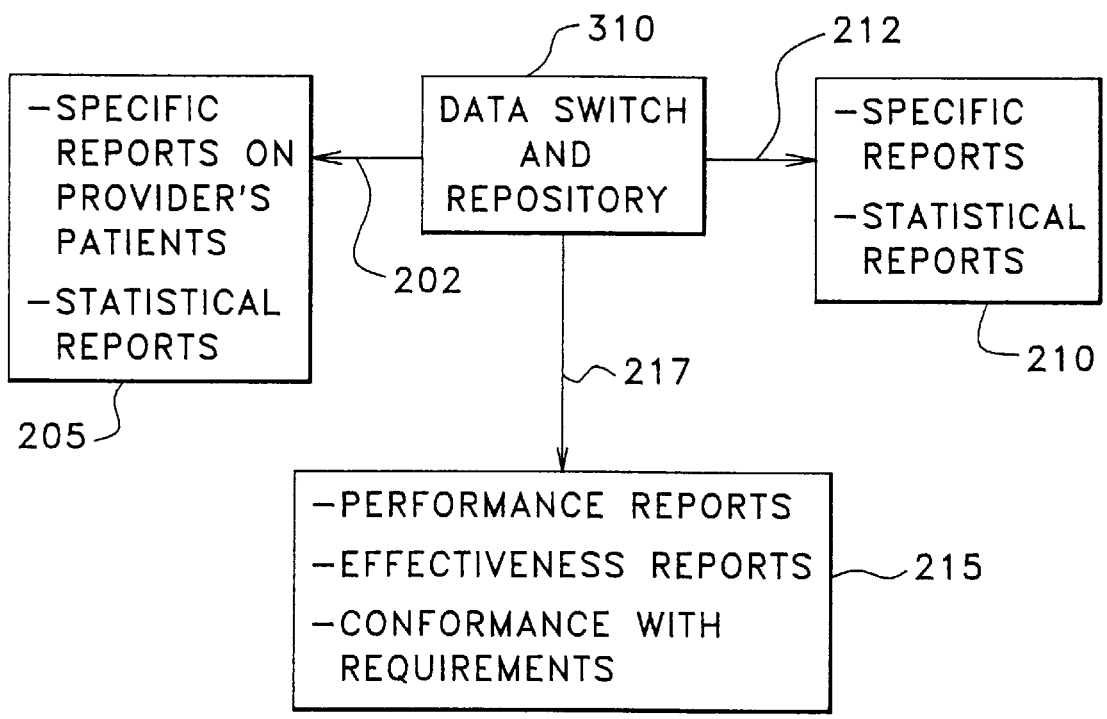
FIG. 4 is a diagram showing data switch and repository reports provided to entities.

The data switch and repository 310 interfaces between all of the other entities (315, 320, 325, 330) of the system via communications lines (312, 322, 327, 332), and maintains records of all of the transactions between entities. Data switch and repository 310 can thus provide reports to the entities based upon statistical analysis of the transactions, as shown in FIG. 4.

The financial institution, or bank, is provided with terminals 315. The bank is responsible for providing an electronic card and credit level to each patient for obtaining health care services. The credit level is determined by how much credit the patient could possibly need in a year, i.e. the deductible, coinsurance and copayments up to where the insurance company starts paying 100%. The patient only loses his or her credit by abusing it (not paying bills). Thus, the bank only informs the health care providers whether the patient has credit or not, and the provider does not have to worry about the amount of credit. The bank pays the health care provider immediately after the provider's claim is adjudicated by the insurance company before collecting from the patient. The insurance company and the patient then each pay their share of the claim to the bank.

Terminals 320 are assigned to health care providers, such as physicians, hospitals, labs or pharmacies, who are members of the health care cooperative. The providers use their terminals to verify that a patient has coverage (verified by the patient's insurance company) and credit (verified by the bank). The credit verification only tells the provider whether the patient's credit is good, not its level. The provider then provides care to the patient and sends an electronic claim to the insurance company. In case a provider does not have one or more terminals, the verification and claim could be done via a credit card "swipe" or even over the phone. The information which must be provided in a verification or claim is much shorter than for conventional claim forms, because so much information about the patient and the provider is already contained in data switch and repository 310.

Once the insurance company adjudicates the claim, the provider is fully reimbursed by the bank for the claim, minus a service charge. The service charge is used to pay for the bank services, the management service, the data switch and repository 310, and a reserve fund for bad patient debt. Thus, the health care provider does not have to worry about the intricacies of the patient's health care coverage, bad debt, slow payment by the insurance company, or the like. The provider's job consists solely of electronically verifying coverage and credit, providing health care, and submitting a simple electronic claim.

The insurance company (or third party payor) terminals 325 are provided to conventional insurance companies, employer self funded insurance trusts (ERISA), government plans, no fault auto insurance plans, and the like. These entities use their terminals to provide verification of patient eligibility to health care providers, to receive claims from providers for adjudication, to tell the bank to pay the claim, and to provide an explanation of benefits to the health care provider. A copy of the explanation of benefits is also mailed to the patient, or can be sent electronically.

For purposes of the present example, the final cooperative group segment is assigned the management service terminals 330. The management service uses its terminals to monitor and manage the cooperative. The management service receives reports from data switch and repository 310, as shown in FIG. 4.

The overall cooperative can readily eliminate duplication of services by the mutual agreement of the various components through the coordinating efforts of the management service 330.

The overall cooperative is based upon a membership which mutually agrees to the agency cooperative business relationship with potentially democratic management thereof. Thus, a network of interdependent agreements make up the cooperative, thereby realizing increased efficiencies and economies of scale while lowering the costs to the members and subscribers. As a result, a managed and collaborative health care marketplace is created that ensures the availability and quality of care in a given locale or region. The cooperative structure can accommodate a single payor, or any third party arrangement, even to the extent of an entire Medicaid or Medicare system as a purchasing member. The arrangement promotes the provision of competitive quality health care services, and the collective well being of the cooperative members.

Figure 3:
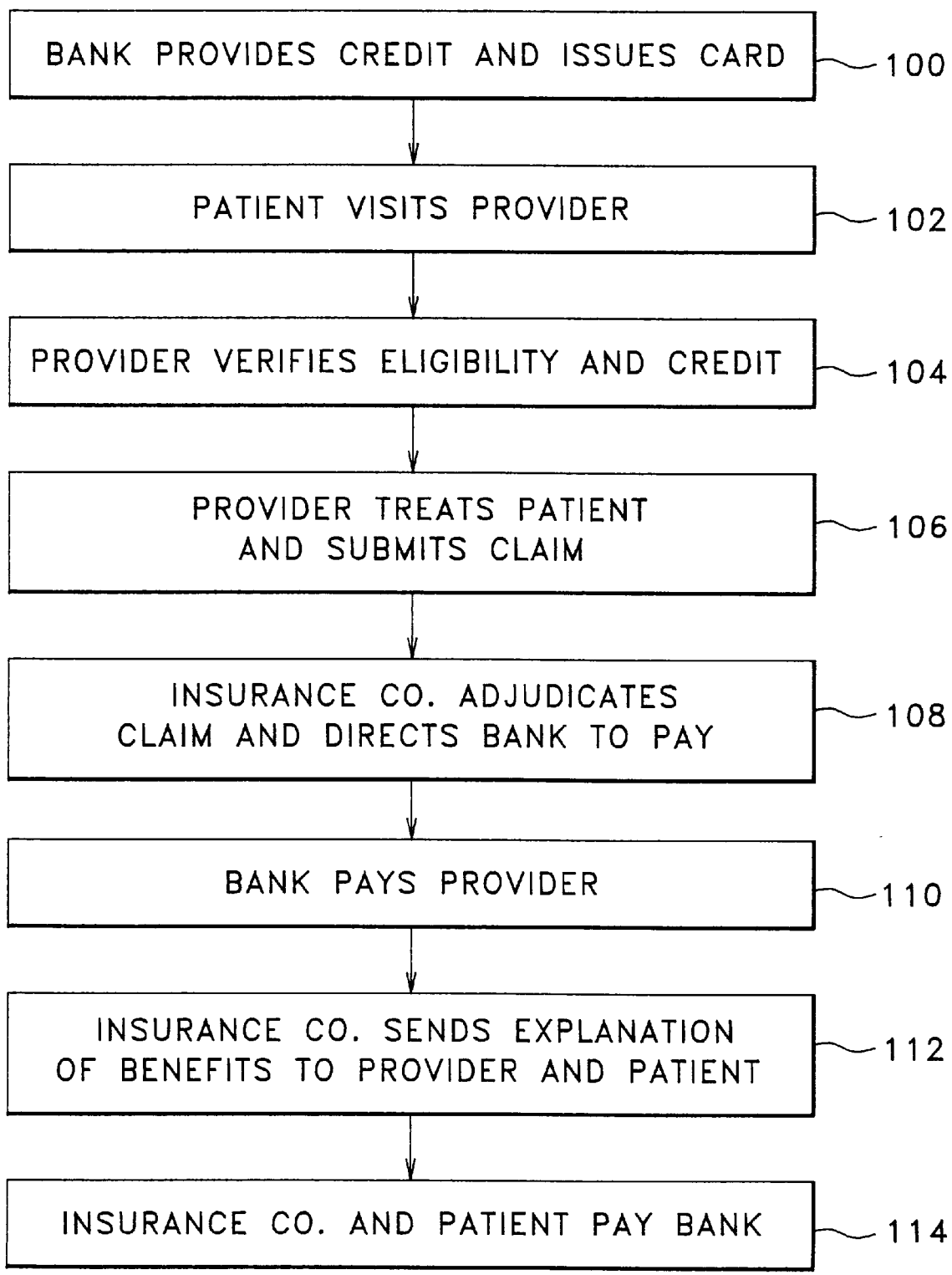
FIG. 3 is a flow diagram of the general steps for establishing eligibility and credit and claim submission and payment.

The FIG. 3 flowchart illustrates the steps followed as a patient uses the services of a health care provider in the cooperative system. Reference to FIG. 2 is helpful in stepping through the flowchart. In step 100, the patient becomes a member of the cooperative. The bank issues the patient an electronic card, and provides a credit level to the patient which would permit the maximum out of pocket expenses which could be accrued by the patient in a year. The bank will verify to providers that the patient has credit, unless the patient does not pay his or her bills, in which case credit is revoked.

In step 102, the patient visits a health care provider, such as a doctor. The doctor verifies in step 104 that the patient has coverage and credit. The doctor may "swipe" the card through a credit card type machine, or may type the patient's identification number into terminal 320. Data switch and repository 310 forwards the eligibility and credit verification request to bank terminal 315. The bank maintains a database of eligibility which is updated by the insurance companies. Data switch and repository 310 records these requests and the responses from the insurance company and bank terminals 325, 315.

If the patient is covered by the insurance company, but does not have credit, the doctor is warned that this patient is likely to default on the doctor's bill, and the bank will not pay it. The doctor can then make the choice of whether to request payment up front, or wait for the insurance company and the patient to pay the bill in the traditional manner.

The doctor provides health care to the patient and submits an electronic claim to the insurance company in step 106. The claim includes diagnostic codes and treatment codes so that the insurance company can adjudicate the claim. The claim is sent from the doctor's terminal 320 to the insurance company terminal 325 via data switch and repository 310, which also records the transaction and the codes.

In step 108, the insurance company adjudicates the claim and directs the bank to pay the doctor. The request is sent from the insurance company terminal 325 to the bank terminal 315 via the data switch and repository, which records the transaction.

In step 110, the bank pays the doctor. The bank pays the claim amount minus a service charge. Generally, electronic funds transfer (ACH type) will be used. In step 112, the insurance company sends an explanation of benefits to the doctor via data switch and repository 310, which records the transaction. The explanation of benefits may be mailed to the doctor as well. The explanation of benefits is also mailed to the patient, and acts as a bill for the patient's share of the claim. In step 114, the patient and the insurance company each pay their share of the claim amount to the bank.

The flow diagram of FIG. 3 has been discussed in terms of the patient seeing a doctor, but visits to other health care providers operate in the same manner. For example, if the patient visited a pharmacy to get a prescription filled, the pharmacist would verify coverage and credit, fill the prescription, and file a claim in the same manner as described above.

FIG. 4 is a diagram showing data switch and repository 310 reports which may be provided to the entities. From the process flow of FIG. 3, it is evident that data switch and repository 310 maintains a database containing every transaction between the entities. Thus, by statistical analysis, it is possible for data switch and repository 310 to generate useful reports based upon these transactions. The reports which data switch and repository 310 generates for each entity depends on what is requested by the entity, and also what the entity is allowed to have in terms of confidentiality.

Block 205 shows the type of reports which might be generated for a health care provider, for example, a doctor. The doctor can access all the details of his or her own patients, including diagnoses, drugs taken, number of visits, and the like. Preferably, the doctor will have to provide both the patients ID number and the doctor's own ID number for access to the information, in order to provide security for the patient's files. The doctor may also access statistical data on all of the patients in the cooperative. Thus, the doctor can find out for all of the patients with a particular condition what drugs were taken, how many doctor visits were necessary for patients taking each drug, etc. It is immediately evident how powerful such statistical reports could be in assessing outcomes and doing cost analysis. Furthermore, the data is automatically collected and maintained, unlike many statistical surveys which rely on doctors exhaustively looking up data, remembering it correctly, and reporting it accurately. Those skilled in the art will appreciate that more complete medical records could also be stored by data switch and repository 310, allowing for more powerful reports.

Block 210 shows the type of reports which might be provided to insurance companies. Again, an insurance company can access detailed data on patients insured with it, and global comparison data among all of the patients in the cooperative. These type of reports help insurance companies assess risk and determine whether a patient is being appropriately treated.

Block 215 shows the type of reports provided to management services. Management services is responsible for monitoring the transaction which take place in the cooperative and ensuring that the entities meet the requirements set by the cooperative. In addition, management services has the role of looking for more efficient and cost effective ways of doing business. The reports provided by data switch and repository 310 are vital in allowing management services to fulfil these responsibilities. For example, management services monitors the performance of each insurance company by checking how long it takes for each company to adjudicate claims and whether each insurance company is paying meritorious claims as determined by the cooperative. Management services can also monitor the comparative effectiveness of health care providers, both in terms of patient outcomes and cost.

The accompanying sixty-seven page Addendum, which is part of the detailed description of the preferred embodiment, provides a detailed definition of the interfaces associated with the present invention. In this Addendum, MSF stands for a master system flowchart, JC is an acronym for the cooperative agency sometimes referred to as Just Care, JCA means the system administrator, JCB means the bank, INS is the insurance company, PRO is the provider, PUR is the purchaser, C is a card, T is a telephone, while "800" indicates a toll-free telephone number, E means electronic, P means paper, TPA/SF indicates a third party administrator and/or self funded member, ECP is an electronics claim processor, and all other initials or abbreviations are believed conventional.

While the exemplary preferred embodiments of the present invention are described herein with particularity, those having normal skill in the art will recognize various changes, modifications, additions and applications other than those specifically mentioned herein without departing from the spirit of this invention.

ADDENDUM

SYSTEM INTERFACE DEFINITIONS
DETAIL INTERFACE DEFINITIONS

| | |
|---|---|
| STEP 1 | PROVIDER CONTRACTS AND PROVIDER DATA BASE |
| | JC arranges Provider Organization Service Agreements to be attached to Provider Membership and Agency Contracts. Provider member organization assists in the distribution of JCB Provider Agreements and JustCare Provider Automatic Deposit Authorization forms. When agreements are complete and information available, JC collects and organizes Payor/Payee data for JCB and individual physician data for JCA. |
| MSF #1 | Approved Physician/Supplier Information for entry into JCA Data Base |
| JC → JCA<br>P/E | JC collects Physician/Supplier information and submits for entry to JCA Data Base, to include:<br>    Physician/Supplier I.D.                                                 Assigned by JCA - 10 Alpha digits<br>    Physician/Supplier Type Code*<br>    Physician/Supplier Name<br>    Physician/Supplier Title<br>    Provider/Payee (Corporate) Name(s)<br>    Provider/Payee (Corporate) Tax I.D. Number(s)<br>    Physician/Supplier I.D's:<br>        Medical License Number<br>        DEA Number<br>        UPIN or Medicare Number (if required by JustCare)<br>        Secondary UPIN Number<br>        Individual Tax I.D. Number/Social Security Number<br>    JustCare Physician/Provider Organization<br>    Specialty 1<br>    Specialty 2 |
| *Note: | Provider Type may be a segmented code with three pieces of information, as follows:<br>a)  A single alpha code representing the Primary Care Setting (G = Group, I = Individual Practitioner, C = Clinic, H = Hospital, etc)<br>b)  A two digit alpha code representing category of primary care (FP = Family Practice)<br>c)  A three digit alpha ccde representing subspecialty care (END = Endocrinology)<br>Locations (1 to n) including Provider/Payee location:<br>    Street Line 1<br>    Street Line 2                                                        multiples to 6<br>    City                                                                 (Will publish 3)<br>    State<br>    Zip<br>    Phone |

ADDENDUM-continued

SYSTEM INTERFACE DEFINITIONS
DETAIL INTERFACE DEFINITIONS

| | |
|---|---|
| MSF #2 | JCA Data Base Information to Providers, Insureds, Purchasers, Agents, etc. |
| JCA ←→ 800<br>T<br>MSF #3a | JCA maintains Physician/Supplier Data Base for directory information and referral calls from other providers, insureds, purchasers, agents, etc.<br>Provider/Payee information to be Provided to JCB by JCA |
| JCA → JCB<br>JCA → JC (PHASE II)<br>E or P | JCA prepares tape, diskette, or other means (medium to be determined by receiving organization) to transfer Provider/Payee File (subset of Physician/Supplier file) information to JCB. Information to include: |

```
                Record Type                              Numeric    (2)
                JCA ID                                   Alpha      (8)
                Provider/Payee ID                        Alpha      (up to 10)
                Provider/Payee Name                      Alpha      (36)
                Primary Mailing Address   Line 1         Alpha      (30)
                City State                               Alpha      (22)
                Zip                                      Numeric    (5)
                Zip Suffix                               Numeric    (4)
                Phone Number                             Numeric    (10)
                A/C/I      A = ACTIVE                    Alpha      (1)
                           C = CHANGE
                           I = INACTIVE
```

| | |
|---|---|
| NOTE: | JC (or JCA) will deliver Provider/Payee JCB Provider Agreements and Provider/Payee Automatic Deposit Authorization forms to JCB by priority mail. JCB adds the following information to their system from the JCB Provider Agreement and Deposit Authorization Approval Form. |

```
                Payee Tax ID (EIN)                       Alpha      (9)
                Bank account number                      Alpha      (17)
                Transroute                               Alpha      (9)
                Faxphone                                 Numeric    (10)
                Signer/Contact                           Alpha      (24)
```

| | |
|---|---|
| MSF #3b | Physician/Supplier Information to be Provided to INS/TPA/SF by JCA |
| JCA → INS/TPA/SF<br>JCA → JC (PHASE II)<br>E | if requested by INS/TPA/SF, JCA will supply Total Provider File (i.e. Physician/Supplier plus Provider/Payee information.<br>Information to include: |

```
                Record Type                              Numeric    (2)
                JCA ID                                   Alpha      (8)
                Provider/Payee or Physician/Supplier ID  Alpha      (10)
                Provider/Payee or Physician/Supplier Type Alpha     (6)
                Provider/Payee or Physician/Supplier Name Alpha     (36)
                Address Line 1                           Alpha      (30)
                City, State ID                           Alpha      (22)
                Zip                                      Numeric    (5)
                Zip Suffix                               Numeric    (4)
                Phone                                    Numeric    (10)
                A/C/I       A = ACTIVE                   Alpha      (1)
                            C = CHANGE
                            I = INACTIVE
                Faxphone                                 Numeric    (10)
                Signer/Contact                           Alpha      (24)
                Provider/Payee Tax ID (EIN OR S.S. No.)  Alpha      (9)
```

| | |
|---|---|
| MSF #4 | Access to JCA JustCare Data Base by JC from On-Line Terminal/PC |
| JCA → JC | for Inquiry, Verification and Reporting |
| E | On-Line Communications are established that enable JC to access information available from JCA Data Base, to include information on<br>    Provider/Payees<br>    Physicians/Suppliers<br>    Utilization Review<br>    Claims<br>    Purchasers, etc.<br>Reporting mechanisms are initiated and run by JC.<br>Printouts from JCA available upon request. |
| MSF #5 | Patient Eligibility and Credit Verification |
| JCB → PRO (PHASE II)<br>E | JCB provides equipment and software to Provider/Payee or assists Provider/Payee with set-up capability (only) for electronic communication w/JCB for online eligibility and credit verification |
| MSF #6 | Medical Claims submission |
| PRO → JCA<br>E | JCA or ECP assists Provider/Payee with set-up capability (only) for electronic communication for Claim Submission |

ADDENDUM-continued

SYSTEM INTERFACE DEFINITIONS
DETAIL INTERFACE DEFINITIONS

| | |
|---|---|
| STEP 2 | JUSTCARE MEMBERS MARKET JUSTCARE COOPERATIVE TO POTENTIAL PURCHASERS |
| | JustCare INS/TPA/SF Members. (Payors) market the JustCare Cooperative through normal channels usually associated with their products. Some INS/TPA/SF members will utilize the services of independent insurance agents. Others may use direct marketing personnel. Third party administrators will inform their employer base directly. Self-funded companies may learn of JustCare through their brokers. |
| | Potential purchaser (employer member) will express interest and additional information will be made available through a proposal (insurance quote) received from the direct marketing representative and/or the independent insurance Agent who has an established relationship with a JustCare Insurance Member. TPAs and self-funded employers (or their broker) will work through a JustCare administrative contract to receive pricing information. |
| | If the potential PUR accepts the insurance proposal, the membership process begins by completion of Insurance Application materials to include: |
| |     Insurance or Administration Application |
| |         JCB Required EFT (Electronic Funds Transfer) Authorization for Premium (if appropriate) |
| |         Insured Enrollment Information, i.e. |
| |             Statement of Insurability |
| |             Enrollment Card |
| |         Premium Deposit Check (estimated first period premium) |
| | Employees complete the following documents for JustCare acceptance: |
| |     JustCare Individual Consumer Member Application and Agreement |
| | Employees receive at this time the JustCare Plan Instruction Packet, which includes a summary of the Articles and Bylaws. |
| | The JustCare INS Member Representative (marketing representative or independent agent) delivers all insurance documents to INS. Either Agent or INS delivers to JustCare the JustCare Individual Consumer Member Application and Agreement. INS Member approves or rejects insurance application. Individual Consumer Retains the second copy (pink). |
| | JC receives from INS or INS Agent the JustCare Individual Consumer Member Application and Agreement from the Purchasing organization; JC separates the original (white) from the copy (yellow); batches and fogs the originals (white) and retains the copy (yellow) for JustCare's records. |
| | \* \* \* \* \* |
| | Since no decision regarding group acceptance is made by TPA/SF organizations, the enrollment process does not have to await acceptance. |
| | TPA/SF representative completes with Purchaser the following: |
| |     Any internal Purchaser acceptance documents |
| |         JCB required EFT (Electronic Funds Transfer) Authorization for Premium (if appropriate). |
| |         Premium Deposit Check if appropriate (estimated first period premium) |
| | The TPA/SF representative is responsible to see that the Employees complete the following JustCare documents: |
| |     JustCare Individual Consumer Member Application and Agreement |
| | TPA/SF agent delivers to JustCare the JustCare Individual Consumer Member Application and Agreement. The Consumer Member retains the second copy (pink) of this form. |
| | JC receives the JustCare Individual Consumer Application and Agreement and separates the original (white) from the copy (yellow). JustCare batches and logs the Individual Consumer Member Application and Agreement, and forwards the original to JCB. The copy (yellow) is retained by JustCare. |
| STEP 2b | ENROLLMENT AND BANK CARD PROCESSING |

DESCRIPTIVE PROCESS FOR PURCHASERS UTILIZING JUSTCARE THROUGH AN INDEMNITY INSURANCE CARRIER:

| | |
|---|---|
| MSF #7 | Selected data Regarding Approved Purchaser Group |
| INS → JCA/JC | |
| INS → JC (PHASE II-Download) | |
| E or P | After Purchaser has been approved by INS, INS provides JC/JCA with select data regarding approved Purchaser, to include: |
| |         \*Group Name (Purchaser) |
| |         \*Group Policy Number |
| |         \*Effective Date (Issue Date) |
| |         \*Number of Employees |
| | \* JCA creates a Master Policyholder File from this information. |
| MSF #8 | Group Data: Purchaser Info., Group I.D., Premiums, Enrollment, Account No.s |
| INS → JCB | |
| INS → JC (PHASE II/Download) | |
| E | INS provides Purchaser Information to JCB via electronic transmission. |

ADDENDUM-continued

SYSTEM INTERFACE DEFINITIONS
DETAIL INTERFACE DEFINITIONS

Purchaser information transmitted by INS to JCB:

| | | |
|---|---|---|
| Record Type | Numeric | (2) |
| JCA ID | Alpha | (8) |
| INS/TPA/SF Name | Alpha | (36)* |
| Group Policy Number | Alpha | (10) |
| Effective Date MMDDYY | Numeric | (6) |
| Primary Mailing Address   Line 1 | Alpha | (30) |
| Primary Mailing Address   Line 2 | Alpha | (30) |
| City State ID | Alpha | (22) |
| Zip | Numeric | (5) |
| Zip Suffix | Numeric | (4) |
| Phone Number | Numeric | (10) |
| Fax Phone Number | Numeric | (10) |
| Payor Cross Reference | Alpha | (20) |

* Transfer of INS Name to JC Card limited to 25 characters

Enrollment Information transmitted by INS to JCB:

| | | |
|---|---|---|
| Record Type | Numeric | (2) |
| JCA ID** | Alpha | (8) |
| INS/TPA/SF ID | Alpha | (10) |
| Insured's Name (Primary Name) | Alpha | (25) |
| Primary Birth Date (MMDDYY) | Numeric | (6) |
| Dependents | Numeric | (2) |
| * Insured's First Line Address | Alpha | (30) |
| * insured's Second Line Address | Alpha | (20) |
| * Insured's City, State ID | Alpha | (22) |
| * Insured's Zip | Numeric | (5) |
| * Insured's Zip Suffix | Numeric | (4) |
| * Insured's Home Phone Number | Numeric | (10) |
| Insured's Social Security | Numeric | (9) |
| Insured's Cert/Subscriber No. | Alpha | (10) |
| Group Policy Number | Alpha | (10) |
| Additional Reference | Alpha | (40) |
| (i.e. subsidiary of purchaser, etc.) | | |
| Cobra Reference | (Alpha) | (1) |
| Primary Care Provider ID | Alpha | (10) |
| CoApp (Spouse) Name | Alpha | (25) |
| CoApp (Spouse) SSN | Numeric | (9) |
| A/C | Alpha | (1) |

A = Add =    Issue Card
    C = Change =  See Step 6 regarding changes which will affect the reissue of a card (same Card Identification Number)

| | | |
|---|---|---|
| Maximum Out of Pocket | Numeric | (S9,2) |

* INS to obtain and transfer to JCB. In the event INS is incapable of providing data elements (*'d) to JCB, JCB will obtain and enter data from Cardholder Agreement.
** NOTE: INS/TPA/SF must supply JCA ID. One INS/TPA/SF may utilize more than one JCA. INS/TPA/SF must send separate batches for separate JCA's to JCB.

| | | |
|---|---|---|
| Tier Rating | Numeric | (1) |

1 = Employee Only
    2 = Employee & Spouse
    3 = Employee & Dependent(s)
    4 = Full Family

| | | |
|---|---|---|
| Effective Date of Coverage | Numeric | Julian Date |
| Credit (Y/N) | Alpha | (1) |
| Eligible (Y/N) | Alpha | (1) |

At this point JCB will have received from JC the JCB Cardholder Application and Agreement. JCB matches with enrollment data downloaded by INS. JCB completes their Insured's Data Base.
JCB assigns identifying information to NEWLY INSURED POPULATION Data Base, to include:

| | | |
|---|---|---|
| JCB/insured Account (Card) Number | Numeric | (16) |

PHASE I NOTE: JCB will make Insured Data Base available to JC upon request.
PHASE II NOTE: When JC has available their own Insured's Data File, it will contain space for a listing of dependents and their eligibility as well. This was projected in order to cover the needs of any HMO's or other organization requiring records on insured lives rather than on insured employees.

\* \* \* \* \* \*

INS will forward to JCB premium payment mechanism for automatic premium withdrawal to be completed by Purchaser. JCB will be responsible for all bank related data in the JCB System. See MSF #8b following:

MSF #8b EFT (Electronic Funds Transfer) Form placed on file with JCB

INS → JCB (PHASE II)
P INS sends to JCB premium payment mechanism (EFT form) for automatic

ADDENDUM-continued

SYSTEM INTERFACE DEFINITIONS
DETAIL INTERFACE DEFINITIONS premium withdrawal completd by Purchaser. JCB will be responsible for the entry of all Purchaser bank related data in the JCB System.

\* \* \* \* \*

DESCRIPTIVE PROCESS FOR SELF FUNDED PURCHASERS OR PURCHASERS UTILIZING JUSTCARE THROUGH A THIRD PARTY ADMINISTRATOR:

MSF #44      Selected Group Data from TPA/SF to JC/JCA

TPA/SF → JCA/JC
TPA/SF → JC (PHASE II-Download)
P

TPA/SF Representative provides JC/JCA (with assistance from JC) select data regarding approved TPA "Account" or SF corporation, to include:
- \*Group Name/Purchaser Name
- \*Group Policy Number, if applicable
- \*Effective Date (Issue Date)
- \*Number of Employees \* JCA creates a Master Policyholder File from this information. Reference MSF #7

NOTE: TPA/SF Representative delivers to JC the following documents:
    JustCare Individual Consumer Member Application and Agreement

MSF #45      Purchaser/Enrollment Data from TPA/SF to JCB

TPA/SF → JCB
TPA/SF → JC (PHASE II-Download)
E

TPA/SF provides Purchaser/Enrollment Information to JCB (with assistance from JC) via electronic transmission. Information to include:

Purchaser information transmitted by TPA/SF to JCB:

| Field | Type | Length |
|---|---|---|
| Record Type | Numeric | (2) |
| JCA ID | Alpha | (8) |
| TPA/SF Group Name | Alpha | (36)* |
| Group Policy Number | Alpha | (10) |
| Effective Date MMDDYY | Numeric | (6) |
| Primary Mailing Address Line 1 | Alpha | (30) |
| Primary Mailing Address Line 2 | Alpha | (30) |
| Purchaser's City State ID | Alpha | (22) |
| Zip | Numeric | (5) |
| Zip Suffix | Numeric | (4) |
| Phone Number | Numeric | (10) |
| Payor Cross Reference | Alpha | (20) |

Enrollment Information transmitted by TPA/SF to JCB:

| Field | Type | Length |
|---|---|---|
| Record Type | Numeric | (2) |
| JCA ID \*\* | Alpha | (8) |
| INS/TPA/SF ID | Alpha | (10) |
| Insured's Name (Primary Name) | Alpha | (25) |
| Primary Birth Date (MMDDYY) | Numeric | (6) |
| Dependents | Numeric | (2) |
| \* Insured's First Line Address | Alpha | (30) |
| \* Insured's Second Line Address | Alpha | (20) |
| \* Insured's City State ID | Alpha | (22) |
| \* Insured's Zip | Numeric | (5) |
| \* Insured's Zip Suffix | Numeric | (4) |
| \* Insured's Home Phone Number | Numeric | (10) |
| Insured's Social Security Number | Numeric | (9) |
| Insured's Cert/Subscriber Number | Numeric | (10) |
| Group Policy Number | Alpha | (10) |

\* TPA/SF to obtain and transfer to JCB. If TPA/SF is incapable of providing data elements (\*'d) to JCB, JCB to obtain from Cardholder Agreement & enter into JCB system.
\*\* NOTE: INS/TPA/SF must supply JCA ID. One INS/TPA/SF may utilize multiple JCA's. INS/TPA/SF must send separate batches for separate JCA's.

| Field | Type | Length |
|---|---|---|
| Additional Reference (i.e. subsidiary of purchaser, etc.) | Alpha | (40) |
| Cobra Reference | (Alpha) | (1) |
| Primary Care Provider I.D. | (Alpha) | (10) |
| CoApp (Spouse) Name | Alpha | (25) |
| CoApp (Spouse) SSN | Numeric | (9) |
| A/C | Alpha | (1) |

A = Add =      Issue Card
    C = Change =    See Step 6 regarding changes which will affect the reissue of a card (same Card Identification Number)

| Field | Type | Length |
|---|---|---|
| Maximum Out of Pocket | Numeric | (S9,2) |
| Tier Rating | Numeric | (1) |

1 = Employee Only
    2 = Employee & Spouse
    3 = Employee & Dependent(s)
    4 = Full Family

| Field | Type | Length |
|---|---|---|
| Effective Date of Coverage | Numeric | Jullan Date |
| Credit (Y/N) | Alpha | (1) |

ADDENDUM-continued

SYSTEM INTERFACE DEFINITIONS
DETAIL INTERFACE DEFINITIONS

|  |  |
|---|---|
|  | Eligible (Y/N)　　　　　　　　　　　　　　　Alpha　　(1) |
|  | TPA/SF Representative delivers to JC the following documents: |
|  | 　JustCare Individual Consumer Member Application and Agreement |
|  | JCB assigns identifying JCB codes to NEWLY INSURED POPULATION, to include: |
|  | 　JCB/insured Account (Card) No.　　　　　　Numeric　(16) |
| PHASE I NOTE: | JCB will make TPA Insured Data Base available to JC upon request for labels, statistical analysis, etc. |
| MSF #45b | EFT (Electronic Funds Transfer) Form placed on file with JCB |
| TPA → JCB (PHASE II) | If appropriate, TPA sends to JCB premium payment mechanism (EFT form) for |
| P | automatic premium withdrawal completd by Purchaser. JCB will be responsible for the entry of all Purchaser bank related data in the JCB System. |
| MSF #9 | JustCare I.D./Bank Card including data on bank card magnetic stripe |
| JCB → PUR | JustCare Card designed by JCB and mailed to Employee Card to contain |
| E/C | the following information: |
|  | Printed Information on front of card: |
|  | 　JustCare (name) |
|  | Printed Information on back of card: |
|  | 　Authorized Signature Line |
|  | 　Credit Instructions from JCB |
|  | 　JCA Telephone Number for Authorization Requests |
|  | 　JCA Name and Address for Claim submission |
|  | Embossed Information: |
|  | 　INS Name or TPA/Employer Name or SF Name |
|  | 　JCB/Insured Account (Card) Number |
|  | 　JCA Identifier (alpha descriptor)* |
|  | 　Insured's Name |
|  | 　　(Spouse's card carries name of Insured) |
|  | 　Insured's Subscriber/Certificate No. (S.S. No.) |
|  | 　Tier Rating or Plan Type |
|  | 　Group Policy Number |
|  | Magnetic Stripe Information: |
|  | 　JCB/Insured Account (Card) Number |
| ** Indicates those items conveyed by JCB as normally on Magnetic Strip |  |
| STEP 3 | PATIENTS ACCESS JUSTCARE SYSTEM USING JUSTCARE CARD; |
|  | CAPTURE OF ENCOUNTER DATA BY JCB |
|  | Patient (Insured or Dependent)/Provider Encounter occurs. |
|  | Patient presents JC Card to Physician/Supplier for identification and eligibility of insurance. |
|  | Three methods of receiving verification of eligibility and authentication of credit status are available to Provider/Payee: |
|  | 　　　1) 800 Number |
|  | 　　　2) Electronic device (terminal or card swipe machine) |
|  | 　　　3) Through referral source |
| NOTE: | The availability of an authorization number provides assurance and convenience to the Provider/Payee and the patient that an authorization inquiry has been made. The information provided at the time of inquiry is "best information available at the point of inquiry" and does not guarantee future credit availability. |
|  | METHOD 1: (800 Number) |
| MSF #10 | 800 Number for Patient Eligibility and Credit Status |
| PRO → JCA | Provider/Payee calls JCA on 800 Number and verbally conveys JCB/insured |
| T | Account (Card) Number and Provider/Payee Name and/or ID. |
| NOTE: | In those situations where a patient may present without the JC Card, Provider/Payee requests from patient the subscriber's name and Social Security Number. This information can be given to JCA in place of the JCB/insured Account (Card) Number. JCA accesses JCB by Insured's Name using the #800 number, and receives Authorization Number if the JCB can match the Insured's Name and Social Security Number. |
| MSF #12 | Patient Eligibility & Credit Status to Answer 800 Number Provider Inquiry |
| JCA ←→ JCB | JCA keys JCB/Insured Account (Card) Number and Provider/Payee Number into PC terminal in order to access JCB. |
| MSF → 13b | Authorization Number Generated by JCB in Response to Provider 800 Number |
| JCB → JCA | Inquiry via JCA |
| E | JCB transmits to JCA terminal the following information: |
|  | 　JCB/Insured Account No. (Card Number) |
|  | 　INS/TPA/SF Name |
|  | 　Group Policy Number |
|  | 　Insured's I.D. (Social Security/Subscriber/Certificate No.) |

ADDENDUM-continued

SYSTEM INTERFACE DEFINITIONS
DETAIL INTERFACE DEFINITIONS

|  |  |
|---|---|
|  | Insured's Name |
|  | Authorization Number (if eligibility = Y) |
|  | (If patient is not <u>eligibleforcoverage</u>, no Authorization |
|  | number will be generated, and a message will read |
|  | "PATIENT NOT ELIGIBLE") |
|  | Credit Status: (SEPARATE LINE ITEM) |
|  | Y = Yes Credit Available to read "CREDIT AVAILABLE" |
|  | N = No Credit Available to read "NO CREDIT AVAILABLE" |
| NOTE: | Because JCB will receive inquiries from various JCA's, it is imperative that the Encounter Data be collected by JCA for return of captured data. Also, for reporting purposes the Authorization Number should be used in conjunction with the JCA ID. |
|  | METHOD 2: (Electronic Device) PHASE II |
| MSF #11 | Card Swipe or Keyed Input for Patient Eligibility and Credit Status |
| PRO ←→ JCB<br>E | Physician/supplier swipes card or keys input into PC terminal direct to JCB. JCB accesses JCB Data Base by Card Number. Electronic equipment used identifies Provider/Payee ID. |
| MSF #13a | Authorization Number Generated by JCB in Response to Card Swipe |
|  | NOTE: THIS OPTION NOT YET DEVELOPED BY JCB. |
| JCB → PRO (PHASE II)<br>E | JCB electronically returns on Printer Box Eligibility, Credit Status & Authorization Number, as follows: |
|  | Insured's Name |
|  | Authorization Number (if Eligibility = Y) |
|  | (If patient is not <u>eligibleforcoverage</u>, no authorization number will be generated and message will read: "PATIENT NOT ELIGIBLE") |
|  | Credit Status (SEPARATE LINE ITEM) |
|  | Y = Yes = JCB Credit is Available to read "CREDIT AVAILABLE" |
|  | N = No = JCB Credit is NOT Available to read "NO CREDIT AVAILABLE" |
|  | Authorization Number Generated by JCB in Response to Keyed Inquiry: |
|  | NOTE: THIS OPTION UNDER REVIEW BY JCB. |
| JCB ←→ PRO (PHASE II)<br>T/E | JCB electronically returns on Provider/Payee's Terminal information regarding Eligibility, Credit Status, and Authorization as follows: |
|  | JCB/Insured Account No. (Card Number) |
|  | INS/TPA/SF Name (whichever is appropriate) |
|  | Group Policy Number |
|  | Insured's Subscriber/Certificate Number |
|  | Insured's Name |
|  | Authorization Number (if Eligibility = Y |
|  | (if patient is not <u>eligibleforcoverage</u>, no Authorization number will be generated, and a message will read "PATIENT NOT ELIGIBLE") |
|  | Credit Status: (SEPARATE LINE ITEM) |
|  | Y = Yes Credit Available to read "CREDIT AVAILABLE" |
|  | N = No Credit Available to read "NO CREDIT AVAILABLE" |
|  | METHOD 3: (Referral Source) |
|  | Referring Provider gives Authorization Number to referring Pharmacy, lab, or x-ray provider with referring order or script. |
| MSF #13c | Authorization Number Conveyed to Provider/Payee from JCB via JCA |
| JCA → PRO<br>T | JCA verbally returns to Provider/Payee on 800 Number the Coverage Status, the Credit Status, and the Authorization Number provided by JCB. |

\* \* \* \* \*

GENERAL NOTES REGARDING AUTHORIZATION PROCESS:

1. JCB responsible for the creation of an 11-digit authorization numbering system which will ultimately convey four pieces of information.
   1) Digit 1: the year of the authorization, by using a single character code (to save space) as follows:
      A = 1995
      B = 1996 etc. to H = 2000
   2) Digit 2: A one character code used for indication of an authorization number that was requested by Provider/Payee).
   3) Characters 3–10: A unique sequential number (00,000,001 to 99,999,999), and
   4) Character 11: the credit status (Yes or No)
      A suggested numbering system might be:
      AJ00000001Y =   A = 1995;
                     P = Authorization Number requested by Provider
         000000000 1 = Sequential Authorization Number
                     Y = Yes Credit Status;
   5) The authorization number will be associated in some reporting instances with the JCA ID (Alpha/Numeric). This will provide several key pieces of data,

ADDENDUM-continued

SYSTEM INTERFACE DEFINITIONS
DETAIL INTERFACE DEFINITIONS including the service area for various out of area claims.
2. if an authorization number is not obtained by the Provider, JCA will request an authorization number from JCB when the claim arrives for repricing by JCA, using the following process:
    a. An attempt is made to find a matching record in the Encounter File, accessing the encounter by Insured's Name or Social Security Number. If the name can be matched to an existing Authorization Number, the number is manually added to the claim.
    b. If claim cannot be matched to an existing Authorization Number in the Encounter File, JCA will request from JCB an Authorization Number in the usual manner. JCA will replace the default "P", with a "J" in the Authorization Number (second digit) and the number manually entered on the claim.
    c. Claims which require an Authorization Number to be added by JCA may be set aside for processing and repricing when the Encounter File containing that Authorization Number has been downloaded by JCB to JCA. JCA will convert the "P" code to a "J" code to the Encounter File at the time of processing and repricing (either from the claim or through some other procedural step).
3. Current JCA computer system can accommodate 11 alpha/numeric digits. The above system allows up to 100 million claims per year.
4. Base authorization numbers may be used more than once by different providers when services are connected to the same encounter.

| | |
|---|---|
| MSF #49 | Authorization Data Captured for Encounter |
| JCB → JCB<br>E | JCB captures the data produced during the electronic access for authorization number through JCB/Insured Account Number. Captured data is stored in an Encounter File for periodic downloading to JCA. (The capture of certain data elements at this point eliminates data entry of those same data elements in the repricing step by JCA). Data elements to be captured include:<br>    Record Type    Numeric  (2)<br>    Authorization Number    Alpha  (11)<br>    Authorization Date    Numeric  (6)<br>    Provider/Payee ID    Alpha  (10)<br>    Insured's Name    Alpha  (25)<br>    Insureds Social Security    Numeric  (9)<br>    Insured's Cert/Subscriber Number)    Alpha  (10)<br>    Insureds Street 1    Alpha  (30)<br>    Insureds Street 2    Alpha  (20)<br>    City, State ID    Alpha  (22)<br>    Zip    Numeric  (5)<br>    Zip Suffix    Numeric  (4)<br>    Date of Birth    Numeric  (6)<br>    Group Policy Number    Alpha  (15)<br>    Additional Reference    Alpha  (40) |
| MSF #50 | Authorization Data Sent by JCB to JCA |
| JCB → JCA<br>JCB → JC (PHASE II-Download)<br>E | JCA receives Encounter data captured by JCB at time of Authorization through periodic downloading (MSF #49). These data elements are retrieved by JCA at time of repricing (by Authorization Number). This step 1) provides accuracy verification of Authorization number, 2) simplifies the process of data entry for JCA and 3) provides JCA with confirmation of Authorization Numbers issued electronically to Provider/Payee (STEP 3, Method 2). |
| NOTE: | JCA (or a National JCA) will maintain the active encounter file. Past files will be archived for periodic analysis. JCB can archive their version of the Encounter File (if desired), based on their own requirements. |
| STEP 3b | AUTHORIZATION FOR HEALTH SERVICES AND REFERRAL |
| | When Physician/Supplier is required to seek U/R approval, the following sequence is followed: |
| MSF #16 | Utilization Criteria Review for Health Services and/or Referral |
| PRO → JCA<br>T | To receive U/R Approval Number Physician/Supplier calls 800 Number at JCA (or other utilization review organization*) and gives JCA the following information:<br>    Physician/Supplier/Identifying Information<br>    Insured's Name<br>    Patient Name (if dependent of Insured)<br>    Group Policy Number<br>    Subscriber Number<br>    Medical information (Dx, Exam, Proc, etc.) as requested by JCA<br>*Payor Members will have the option of selecting their own utilization review body. |
| MSF #16b | U/R Approval or indication of Benefits Status (i.e. not covered, restrictions, etc.) |
| JCA → PRO<br>T | JCA conveys during telephone interview with Physician/Supplier that approval for medical procedure or hospital admission is granted or informs Physician/Supplier of any existing restriction. |

ADDENDUM-continued

SYSTEM INTERFACE DEFINITIONS
DETAIL INTERFACE DEFINITIONS

| | |
|---|---|
| MSF #17 | U/R Approval Number for Health Services or Referral |
| JCA → PRO<br>T | JCA evaluates medical information based on pre-determined criteria. JCA indicates approval or Benefit Status (i.e. not covered, restrictions, etc.). JCA issues U/R Approval Number to Physician/Supplier by phone and captures in JCA computer system. |
| MSF #17b | U/R Approval Number Sent with Claim |
| PRO → JCA<br>P | Provider/Payee includes U/R Approval Number on Claim when submitted (mailed) to JCA |
| MSF #18 | U/R Approval Number Sent with Claim |
| JCA → INS/TPA<br>P | JCA sends UIR Approval Number to INS/TPA w/Claim & Repricing Sheet. |
| Note: | The U/R Approval number to be designed so that it is distinct from the JustCare Authorization Number, in the following way:<br>P + 000001 (P = Physician = Outpatient)<br>H + 000001 (H = Hospital = Inpatient) |
| STEP 3c | PATIENT WITH JUSTCARE CARD ACCESSES NONPARTICIPATING PROVIDER; |
| | CLAIMS AND PAYMENTS |
| | Since the JustCare Card is available for non-participating physicians and other providers to verify eligibility only, JCA and JCB will need to be able to accommodate these types of calls. To do so, JCB will establish a unique Provider Number only for the purpose of assigning authorization numbers. (Approved by JCB 10/12/94).<br>When JCA receives a call from a non-participating provider, JCA will enter that unique Provider ID along with the JC Card Number. If the JustCare insured is eligible for coverage, the Authorization number will be supplied to the non-participating provider and the available data captured for the Encounter Data download. |
| MSF #19 | 800 Number for Coverage Verification. |
| NONPAR PRO → JCA<br>T | Non-participating Provider calls National JCA 800 Number for information relative to coverage verification. Non-participating Provider gives to JCA the JCB/Insured Account (Card) Number and Provider Name. |
| MSF #19b | JCA contacts JCB via terminal for eligibility of coverage. |
| JCB → JCA<br>T/E | (same as MSF #12, #13b and 13c)<br>JCA keys Card Number into PC terminal in order to access JCB. JCB transmits to JCA terminal the following information:<br>    JCB/Insured Account No. (Card Number)<br>    INS/TPA/SF Name (whichever is appropriate)<br>    Group Policy Number<br>    Insured's Subscriber/Certificate Number<br>    Insured's Name<br>    Authorization Number (if Eligibility = Y)<br>    (if patient is noteligibleforcoverage, no Authorization number will be generated and a message will say "PATIENT NOT ELIGIBLE"<br>    Credit Status (SEPARATE LINE ITEM)<br>    Y = Yes = JCB Credit is Available to read "CREDIT AVAILABLE"<br>    N = No = JCB Credit is NOT Available to read "NO CREDIT AVAILABLE" |
| MSF #20 | Authorization Number for Coverage Only |
| JCA → NONPAR PRO<br>T | JCA gives Verification of Eligibility and Authorization Number to Non-Participating Provider for non-participating claim*.<br>*Credit status not available for non-participating service. |
| MSF #20a | Patient Sends Non-Participating Claim to JCA |
| Patient → JCA<br>P | Having paid (or made arrangements for direct pay) the Non-Participating Provider, the patient receives a hard copy claim from the Non-Participating Provider. Patient submits claim to JCA with paid receipt (if applicable).<br>* * * OR * * * |
| MSF #20b | Non-Participating Provider Receives Assignment and sends Claim with<br>Authorization Number to JCA |
| NONPAR PRO → JCA<br>P | Non-Participating Provider may request assignment and take responsibility for Claim Submission to JCA. Non Participating Provider includes Authorization Number on claim, if obtained. |
| MSF #20c | JCA Submits Non-Participating Claim to INS/TPA/SF |
| JCA → INS/TPA/SF | JCA receives Non-Participating claim from patients and Non-Participating |

ADDENDUM-continued

SYSTEM INTERFACE DEFINITIONS
DETAIL INTERFACE DEFINITIONS

| | |
|---|---|
| P | Providers, captures basic claim data, and forwards without repricing to INS. |
| STEP 3d | PATIENT (NEW TO PROVIDER) ACCESSES JUSTCARE PROVIDER |
| | WITHOUT JC CARD; CLAIMS AND PAYMENTS |
| | Where an unknown Patient fails to present a JustCare Card at the time of treatment, the Provider/Payee may request payment at the time of treatment and/or bill the patient directly. |
| | Having paid (or made arrangments for direct pay) the Provider/Payee, the patient receives a hardcopy claim from the Provider/Payee. Patient submits claim to JCA with paid receipt. |
| MSF #23 | Claim and Re-Pricing Sheet Prepared by JCA |
| JCA → INS/TPA/SF | JCA receives claim from patient, captures all pertinent claim data, and reprices |
| P/E | the claim. JCA forwards claim (paper or electronic) and Claim Charge Sheet (Repricing Cover Sheet) to INS/TPA/SF. U/R Approval number (if appropriate) may also be sent to INS, depending upon the U/R procedures in place with INS. |
| NOTE: | Refer to Step 4 for a more indepth description of JCA's role to reprice ctaim, collect U/R data and forward claim to INS. |
| | "Patient Submitted" Claims are adjudicated by INS; payment determined, and Patient reimbursed by INS/TPA/SF when EOB is sent to Patient. INS/TPA/SF submits EOB as Paid to Provider. Provider reimburses overpayments previously collected from patient (or balance bills patient as appropriate). |
| MSF #21 | INS/TPA/SF Sends EOB Summary Data to JC |
| INS/TPA/SF → JC | INS/TPA/SF is responsible for sending EOB summary data regarding transaction |
| INS/TPA/SF → JC | to JC. EOB data may be sent at time of processing EOB as an additional copy |
| (PHASE II-Download) | to JC. Jn PHASE II, information may be sent as a daily download. |
| P | EOB information to include: |
| |     Date of Transaction (ACH Date) |
| |     Date of Service |
| |     Group Policy Number |
| |     Provider/Payee Name |
| |     Provider/Payee Tax ID |
| |     Insured Name |
| |     Insured's Certificate Number |
| |     Patient Name |
| |     Patient Social Security (if available) |
| |     EOB/Claim Number |
| |     Billed Charges Amount |
| |     Appropriate Discounts |
| |     Exclusions: COB, etc. |
| |     Insurance Pay Portion |
| |     Patient Pay Portion |
| |     Non Covered Charges |
| NOTE: | Should the Physician/Supplier attempt to determine eligibility of the unknown patient through the JCA and eligibility/credit is determined, the Provider/Payee may proceed with submission of claim as in STEP 4. |
| STEP 4 | SUBMISSION AND PRE-PROCESSING OF "YES" COVERAGE/"YES" CREDIT |
| | CLAIMS AND "YES" COVERAGE/"NO" CREDIT CLAIMS |
| | Having treated a patient (Insured or Dependent), The Provider/Payee submits claim to JCA, regardless of the credit status rating given in the Authorization process. |
| MSF #22 | Claim Submission by Provider/Payee with Authorization Number and |
| PRO → JCA | Utilization Review Approval |
| P/E | Provider sends claim (paper or electronic) to JCA, to include all typical claim information plus: |
| |     Authorization Number, if obtained, and |
| |     U/R Approval Number, if appropriate |
| | Authorization signature for Insured to assign benefits remains on file with PRO. |
| MSF #23 | Preprocessing of Claim and Repricing Sheet |
| JCA → INS/TPA/SF | |
| JCA → JC (PHASE I-Hardcopy monthly summary of repriced claim data) | |
| JCA → JC (PHASE II-Download) | |
| P/E | JCA receives claim, captures all pertinent claim data, and reprices claim. JCA forwards Claim (Paper or Electronic) and Claim Charge Sheet (Repricing Cover Sheet) to INS/TPA/SF, to include Authorization Number (regardless of credit status). U/R Approval Number, if appropriate, may also be forwarded to INS/TPA/SF depending upon their requirements. |

ADDENDUM-continued

SYSTEM INTERFACE DEFINITIONS
DETAIL INTERFACE DEFINITIONS

| | |
|---|---|
| STEP 5 | PROCESSING AND ELECTRONIC PAYMENT OF "YES CREDIT" CLAIMS |
| MSF #24 and #25 | INS Notifies JCB of Insurance Pay Portion and Patient Pay Portion |
| INS/TPA/SF → JCB<br>INS/TPA/SF → JC (PHASE II)<br>E | Having adjudicated the claim INS/TPA/SF transmits to JCB the "Post Adjudication Claim Payment Data (Charges)" which contain the Insurance Pay and Patient Pay information as follows:<br><br>Record Type — Numeric (2)<br>INS/TPA/SF ID* — Alpha (10)<br>Group Policy Number — Alpha (9)<br>EOB/Claim No. — Alpha (15)<br>Insured's Social Security No. — Alpha (9)<br>Insured's Cert/Subscriber No. — Alpha (10)<br>Insured's Name — Alpha (25)<br>Patient Pay Amount — Numeric (S9,2)<br>Insurance Pay Amount — Numeric (S9,2)<br>Patient Name — Alpha (25)<br>Patient Social Security — Numeric (9)<br>Patient Cert/Subscriber No. — Alpha (10)<br>Date of Service — Numeric (6)<br>Physician/Supplier Name — Alpha (36)<br>Provider/Payee Tax ID (EIN or SS) — Alpha (9) |
| * For JC purposes. Number to be assigned by JC to INS/TPA/SF. May consist of JC in-house Member Number. | |
| NOTE 1: | JCB generates a confirmation fax to INS summarizing the funding request, followed by a mailed confirmation. The detail of these documents is not currently available (12/1/94). |
| NOTE 2: | JCB validates the Patient Pay Portion against the Insured's bank credit limit. If the patient pay transaction is within the credit limits allowed by JCB, and if the patient has maintained a "Yes Credit" rating from the point of service, JCB transfers the funds as directed by INS/TPA/SF.<br>If the patient pay portion exceeds the credit limits allowed by JCB or if patient has "lost credit", JCB follows the procedure described in Step 5d. |
| MSF #26 & 27 | Patient Pay Amount and Insurance Pay Portion paid through JCB Bank |
| JCB → PRO | Account: EFT to Provider/Payee Bank |
| E | Having received funding for INS Pay Portion from INS/TPA/SF and having approved "Insured's credit" at the transactional level, JCB transmits to Provider/Payee Bank Account the Insurance Pay Portion AND Patient Pay Portion Dollar Amount (if credit is yes).<br>JCB collects from one day's activity all transactions to be transferred to each Provider/Payee into one sum total. JCB faxes Notice of Transfer to Provider/Payee the day of the funding. Provider/Payee typically would receive funds the next day. Notice of Transfer to include the following items:<br>    Provider/Payee Name<br>    Total Amount of Transfer<br>    Bank Account where funds deposited<br>JCB mails Enhanced Funds Transfer Notification to Provider/Payee for each day's transactions, to include: |
| Header Information: | Provider/Payee Name<br>Provider/Payee Address<br>Provider/Payee Tax ID<br>Bank Account Number where funds deposited |
| Line Item information: | Date of Transaction<br>Date of Service<br>Patient Name<br>Patient Social Security Number<br>Insureds Name<br>Policyholder Group Number<br>Insureds Certificate/Subscriber Number<br>Payor of Insurance Pay Portion (INS/TPA/SF)<br>EOB Claim Number<br>Physician/Supplier Name<br>Gross Amount of Each Transaction<br>    Amount of JustCare Discount<br>    Amount of Insurance Pay Portion<br>    Amount of Patient Pay Portion Disbursed to Provider<br>        through JC Cardholder Account<br>    Amount of Provider Discount<br>    Net Payment Amount |

PHASE II: With electronic capability at the Provider/Payee's location, JCB may convert the Notice by Mail to a electronic download process.

The following information is captured by date for download to JC:
Date of Transaction

ADDENDUM-continued

SYSTEM INTERFACE DEFINITIONS
DETAIL INTERFACE DEFINITIONS

|  |  |
|---|---|
|  | Date of Service |
|  | Provider/Payee JCA ID |
|  | Insureds JCA ID |
|  | Policyholder Group Number |
|  | EOB/Claim Number |
|  | Insured's Name |
|  | Insured's Certificate/Subscriber Number |
|  | Patient Name |
|  | Patient Social Security (if available) |
|  | Provider/Payee Name |
|  | Provider/Payee Tax ID |
|  | Physician/Supplier Name |
| MSF #54 | JC Notifies JCB of Collected Patient Pay Accounts for Transfer to |
| JC → JCB | Provider/Payee |
| P/E (PHASE II) | Once JC collects (through JC Collection Agency) Patient Payments after assignment by Provider/Payee, JC may notify JCB of amounts held in JC collection account for transfer by JCB to Provider/Payee Account. |
| MSF #55 | Patient Pay Amount From JC Collection Account to Provider/Payee by JCB |
| JCB → PRO (PHASE II) E | JCB electronically transfers amounts paid by Patient from JC collection account to Provider/Payee Account, faxes/mails confirmation of deposit to Provider/Payee; and collects data for monthly Provider Account Activity Statement (See MSF #26, STEP 5 and 5c). |
|  | \* \* \* \* \* \* |
|  | If JC is unable to collect payment from Patient, the uncollected account is returned to Provider as a write-off. |
| NOTE 2: | SHOULD A SITUATION OCCUR WHERE THE CREDIT STATUS CHANGES BETWEEN THE POINT OF SERVICE AND THE ACCOUNTING TRANSACTION MADE BY JCB, JCB WILL PROCESS TRANSACTION WITH CREDIT INFORMATION AVAILABLE AT TIME OF TRANSACTION TRANSFER. |
|  | a) IF CREDIT CHANGES FROM "YES" TO "NO", PROVIDER/PAYEE WILL HAVE TO BALANCE BILL THE INSURED FOR ANY AMOUNT REMAINING DUE. |
|  | b) IF CREDIT CHANGES FROM "NO" TO "YES", BANK WILL TRANSFER THE PATIENT PAY PORTION FROM JCB'S FUNDS TO THE PROVIDER. SHOULD THIS RESULT IN AN OVERPAYMENT TO PROVIDER (BECAUSE THE PROVIDER/PAYEE APPROPRIATELY COLLECTED FUNDS FROM A "NO CREDIT" PATIENT), THE PROVIDER/PAYEE WILL REFUND OVERPAYMENT TO INSURED. |

The method of notification of "No Credit" Transactions to JC by JCB will change as the volume of "no credit" transaction increases, as follows:

| PHASE I: | Faxed information plus notation on JCB Claims Summary Account Statement (MSF #30) |
|---|---|
| PHASE II: | Download information plus plus notation on JCB Claims Summary Account Statement (MSF #30) |
| STEP 5e | ACCESS TO JUSTCARE RESERVE ACCOUNT BY JCB AND BAD DEBT |

COLLECTION

A. After monthly billing to Insured by JCB (see MSF #48 - STEPS 5 and 5c), the following billing sequence is established by JCB:
    1) Initial billing provides 30 days for receipt of payment without interest or finance charges.
    2) If Full or Required Payment\* is not received by Due Date, JCB sends second billing at 30 days, with interest and/or finance charges added, giving a Final Due Date (an additional 30 days past the second billing).
    \* If Required Payment is less than $25, $25 is the Required Payment B. If full or partial payment is not received by Final Due Date, JCB transfers responsibility for Debt Collection to JC at 90 days. This will be done by batch processing to coincide with Final Due Date Notices. The Insured's hard copy file will be turned over to JC to include:
    1) Name and demographic data of Insured
    2) Insured Statement Activity (historical) giving the detail of all patient encounters not paid
    3) Total Balance Due plus Interest and Finance Charges
    4) Collection process incurred by JCB
       (a) Date Notices given
       (b) Content of Notices given (i.e Standard Letter #2, etc.)
       (c) Collection history (i.e. phone conversations, etc)
       (d) Whether or not there is an alleged dispute
    5) A hard copy Credit Bureau Report
       Note: JC will determine whether or not the Account should be turned to Collection or should be charged against the JC Reserve as a "can't pay"
               Gross Amount of Each Transaction

ADDENDUM-continued

SYSTEM INTERFACE DEFINITIONS
DETAIL INTERFACE DEFINITIONS

|  |  |
|---|---|
| | Amount of JustCare Discount |
| | Amount of Insurance Pay Portion |
| | Amount of Patient Pay Portion Disbursed to Provider |
| |     through JC Cardholder Account |
| | Amount of Provider Discount |
| | Net Payment Amount |
| [TO BE DETERMINED] | Amount Denied Credit - Referred back to Provider for Collection |
| MSF #48 | JCB Bills Patient for Patient Pay Portion |
| | |
| JCB → Insured | JCB sends a monthly statement to Insured, showing claim activity |
| P | Information to include: |
| |     JCB/Insured Account (Card) Number |
| |     Insured's (CardHolder) Name |
| |     Insured's (CardHolder) Address, Zip |
| |     Date of Transaction |
| |     Date of Service |
| |     Line Item Description, to include |
| |         EOB/Claim Number |
| |         Patient First Name |
| |         Physician/Supplier Name |
| |     Patient Pay Dollar Amount |
| |     Payment since Last Statement |
| |     Minimum Payment |
| |     Terms of Payment |
| |     Balance Due |
| |     Payment Due Date |
| Concurrently: | |
| MSF #21 | INS/TPA/SF Produces EOB and Distributes to Provider & Patient |
| | |
| INS/TPA/SF → PRO/PATIENT | INS/TPA/SF prepares EOB (Explanation of Benefits) and sends copies to PRO |
| P | and Patient. |
| MSF #31 | INS/TPA/SF Forwards EOB Data to JC |
| | |
| INS/TPA/SF → JC/JCA | |
| INS/TPA/SF → JC (PHASE II-Download) | |
| P | INS/TPA/SF is responsible for sending EOB summary data regarding transaction |
| | to JC. EOB data may be sent at time of processing EOB as an additional copy |
| | to JC. In PHASE II, information may be sent as a daily download. |
| | EOB Information to Include: |
| |     Date of Transaction (ACH Date) |
| |     Date of Service |
| |     Group Policy Number |
| |     Provider/Payee Name |
| |     Provider/Payee Tax ID |
| |     Insured Name |
| |     Insured's Certificate Number |
| |     Patient Name |
| |     Patient Social Security (if available) |
| |     EOB/Claim Number |
| |     Billed Charges Amount |
| |     Appropriate Discounts |
| |     Exclusions: COB, etc. |
| |     Insurance Pay Portion |
| |     Patient Pay Portion |
| |     Non Covered Charges |
| STEP 5b | PROCESSING AND ELECTRONIC PAYMENT OF "NO" CREDIT CLAIMS AND |
| | PAYMENTS |
| | |
| MSF #24 & 25 | INS Notifies JCB of Insurance Pay Portion and Patient Pay Portion |
| | |
| INS/TPA/SF → JCB | Having adjudicated the claim, INS/TPA/SF transmits to JCB the "Post |
| INS/TPA/SF → JC (PHASE II) | Adjudication Claim Payment Data (Charges)," which contain the Insurance Pay |
| E | Portion and Patient Pay Portion information as follows: |
| |     Record Type    Numeric   (2) |
| |     INS/TPA/SF ID*    Alpha   (10) |
| |     Group Policy Number    Alpha   (10) |
| |     EOB/Claim Number    Alpha   (15) |
| |     Insured's Social Security    Numeric   (9) |
| |     Insured's Cert/Subscriber Number    Numeric   (10) |
| |     Insured's Name    Alpha   (25) |
| |     Patient's Name    Alpha   (10) |
| |     Patient Social Security    Alpha   (10) |
| |     Patient Cert/Subscriber Number    Numeric   (9) |
| |     Date of Service    Numeric   (6) |
| |     Physician/Supplier Name    Alpha   (36) |

ADDENDUM-continued

SYSTEM INTERFACE DEFINITIONS
DETAIL INTERFACE DEFINITIONS

|  |  |  |  |
|---|---|---|---|
|  | Provider/Payee I.D. (EIN or S.S.) | Alpha | (10) |
|  | Patient Pay Amount | Numeric | (S9,2) |
|  | Insurance Pay Amount | Numeric | (S9,2) |

\* For JC purposes. Number to be assigned by JC to INS/TPA/SF. May consist of JC in-house Member Number.

NOTE 1: JCB generates a confirmation fax to INS summarizing the funding request, followed by a mailed confirmation. If the transfer is not possible, JCB conveys to INS/TPA/SF the following information:
- Name of INS/TPA/SF
- Group Policy Number
- Insured's Name
- Insured's Social Security Number
- Insured's Cert/Subscriber Number
- Patient Pay Amount
- Insurance Pay Amount
- Provider/Payee Tax ID
- Reason for inability to transfer funds NOTE 2: JCB validates the Patient Pay Portion against the Insured's bank credit limit. Since there was no credit available at time of Authorization, the assumption is that no credit will be available at time of transaction. JCB follows the procedure described in STEP 5d, MSF #53.

MSF #27: Insurance Pay Amount from INS/TPA/SF ACH Account: EFT to Provider/Payee JCB → PRO    Bank E    Having received funding for INS Pay Portion from INS/TPA/SF, JCB transmits to Provider/Payee Bank Account the InsurancePayPortion.
JCB adds to Provider's daily activity record all transactions to be transferred to that Provider/Payee that represent INS/TPA/SF payments only. JCB faxes Notice of Transfer to Provider/Payee the day of the funding. Provider/Payee receives funds the following day (normally). Notice of transfer to include:
- Provider/Payee Name
- Total Amount of Transfer
- Bank Account Number where funds deposited JCB mails Enhanced Funds Transfer Notification to Provider/Payee for each day's transactions, to include Header Information:
- Provider/Payee Name
- Provider/Payee Address
- Provider/Payee Tax ID
- Bank Account Number where funds deposited Line Item Information:
- Date of Transaction
- Date of Service
- Patient Name
- Patient Social Security Number
- Insureds Name
- Policyholder Group Number
- Insureds Certificate/Subscriber Number
- Payor of Insurance Pay Portion (INS/TPA/SF)
- EOB Claim Number
- Physician/Supplier Name Gross Amount of Each Transaction
- Amount of JustCare Discount
- Amount of Insurance Pay Portion
- Amount of Patient Pay Portion Disbursed to Provider through JC Cardholder Account
- Amount of Provider Discount
- Net Payment Amount PHASE II: With electronic capability at the Provider/Payee's location, JCB may convert the Notice by Mail to a electronic download process.

The following information is captured by date for download to JC:
- Date of Transaction
- Date of Service
- Provider/Payee JCA ID
- Insureds JCA ID
- Policyholder Group Number
- EOB/Claim Number
- Insured's Name
- Insured's Certificate/Subscriber Number
- Patient Name
- Patient Social Security (if available)
- Provider/Payee Name
- Provider/Payee Tax ID
- Physician/Supplier Name
- Gross Amount of Each Transaction
    - Amount of JustCare Discount
    - Amount of Insurance Pay Portion

ADDENDUM-continued

SYSTEM INTERFACE DEFINITIONS
DETAIL INTERFACE DEFINITIONS

| | |
|---|---|
| | Amount of Patient Pay Portion Disbursed to Provider through JC Cardholder Account |
| | Amount of Provider Discount |
| | Net Payment Amount |
| [TO BE DETERMINED] | Amount Denied Credit - Referred back to Provider for Collection |
| Concurrently: | |
| MSF #21 | INS/TPA/SF Produces EOB and Distributes to Provider & Patient Line Item |
| Information: | |
| INS/TPA/SF → PRO/PATIENT | INS/TPA/SF prepares EOB (Explanation of Benefits) and sends copies to PRO |
| P | and Patient. |
| MSF #31 | INS Forwards EOB Data to JC |
| INS/TPA/SF → JC/JCA | INS/TPA/SF is responsible for sending EOB data regarding transaction to JC. |
| INS/TPA/SF → JC (PHASE II-Download) | EOB data may be sent at time of processing EOB as an additional copy to JC. |
| P | In PHASE II, information may be sent as a daily download. |
| | EOB Information to Include: |
| |     Date of Transaction (ACH Date) |
| |     Date of Service |
| |     Group Policy Number |
| |     Provider/Payee Name |
| |     Provider/Payee Tax ID |
| |     EOB (Claim) Number |
| |     Insured Name |
| |     Insured's Certificate Number |
| |     Patient Name |
| |     Patient Social Security (if available) |
| |     Billed Charges Amount |
| |     Appropriate Discounts |
| |     Exclusions: COB, etc. |
| |     Insurance Pay Portion |
| |     Patient Pay Portion |
| |     Non Covered Charges |
| STEP 5c | INSURANCE PAYMENT ALTERNATIVE: |
| | DIRECT PAYMENT TO PROVIDER BY INS/TPA/SF |
| | PROCESSING OF PATIENT PAY BY JUSTCARE BANK |
| | JustCare will provide an option whereby an INS/TPA/SF may request to use the JustCare Card for the patient pay portions, but elects to send INS/TPA/SF portion directly to the Provider. If this were to occur, the standard JustCare procedures would be utilized, except that the INS/TPA/SF would forward only patient pay portion notification to JCB. |
| NOTE: | Patient Pay Portions are subject to the same Administrative Fee charges identified in the Appendix. Insurance Pay Portions would be subject to an access fee calculated and paid by INS/TPA/SF directly to JC. [TO BE DETERMINED] |
| | \* \* \* \* \* \* |
| | After receipt of and adjudication of claims, INS/TPA/SF processes the Insurance Pay Portion manually through their own internal accounting and check writing processes. The PatientPayPortionOnly is forwarded to JCB for processing as follows: |
| MSF #25 | INS/TPA/SF Notifies JCB of Patient Pay Portion |
| INS/TPA/SF → JCB | INS/TPA/SF transmits to JCB the "Post Adjudication Claim Payment Data |
| INS/TPA/SF → JC (PHASE II-Download) | (Charges)", which includes Patient Pay Information as following: |
| E | |

| | | |
|---|---|---|
| Record Type | Numeric | (2) |
| INS/TPA/SF ID* | Alpha | (10) |
| Group Policy Number | Alpha | (10) |
| EOB/Claim Number | Alpha | (15) |
| Insured's Social Security | Numeric | (9) |
| Insured's Cert/Subscriber No. | Alpha | (10) |
| Insured's Name | Alpha | (25) |
| Insurance Pay Amount | Numeric | (S9,2) |
| (Insur Pay Amount will always be $0.00 when INS/TPA/SF processes Insurance Payments manually) | | |
| Patient Pay Amount | Numeric | (S9,2) |
| Patient Name | Alpha | (25) |
| Patient Social Security | Numeric | (9) |
| Patient Cert/Subscriber No. | Alpha | (10) |
| Date of Service | Numeric | (6) |
| Physician (Supplier Name) | Alpha | (36) |
| Provider/Payee I.D. (EIN or S.S.) | Alpha | (9) |

\* For JC purposes. Number to be assigned by JC to INS/TPA/SF. May consist of JC in-house Member Number.

ADDENDUM-continued

SYSTEM INTERFACE DEFINITIONS
DETAIL INTERFACE DEFINITIONS

| | |
|---|---|
| NOTE: | JCB validates the Patient Pay Portion against the Insured's bank credit limit. If the patient pay transaction is within the credit limits allowed by JCB, and if the patient has maintained a "Yes Credit" rating from the point of service, JCB proceeds with the transaction.<br>If the patient pay portion exceeds the credit limits allowed by JCB or if patient has "lost credit", then JCB follows the procedure described in STEP 5d. |
| MSF #26 | Patient Pay Amount Advanced from JCB Bank Account: EFT to Provider/Payee Bank |
| JCB → PROE | Having received the funding for the INS Pay Portion from INS/TPA/SF and having approved the "Insured's credit" at the transactional level, JCB transmits to Provider/Payee Bank Account the Patient Pay Portion Dollar Amount.<br>JCB collects from one day's activity all transactions to be transferred to each Provider/Payee into one sum total. JCB faxes Notice of Transfer to Provider/Payee the day of the funding. Provider/Payee typically would receive funds the next day. Notice of Transfer to include the following items:<br>    Provider/Payee Name<br>    Total Amount of Transfer<br>    Bank Account where funds deposited<br>JCB mails Enhanced Funds Transfer Notification to Provider/Payee for each day's transactions, to include: |
| Header Information: | Provider/Payee Name<br>Provider/Payee Address<br>Provider/Payee Tax ID<br>Bank Account Number where funds deposited |
| Line Item Information: | Date of Transaction<br>Date of Service<br>Patient Name<br>Patient Social Security Number<br>Insureds Name<br>Policyholder Group Number<br>Insureds Certificate/Subscriber Number<br>Payor of Insurance Pay Portion (INS/TPA/SF)<br>EOB Claim Number<br>Physician/Supplier Name<br>Gross Amount of Each Transaction<br>    Amount of JustCare Discount<br>    Amount of Insurance Pay Portion<br>    Amount of Patient Pay Portion Disbursed to Provider<br>        through JC Cardholder Account<br>    Amount of Provider Discount<br>    Net Payment Amount |
| PHASE II: With electronic capability at the Provider (Payee's location, JCB may convert the Notice by Mail to a electronic download process. | |
| | The following information is captured by date for download to JC:<br>    Date of Transaction<br>    Date of Service<br>    Provider/Payee JCA ID<br>    Insureds JCA ID<br>    Policyholder Group Number<br>    EOB/Claim Number<br>    Insured's Name<br>    Insured's Certificate/Subscriber Number<br>    Patient Name<br>    Patient Social Security (if available)<br>    Provider/Payee Name<br>    Provider/Payee Tax ID<br>    Physician/Supplier Name<br>    Gross Amount of Each Transaction<br>        Amount of JustCare Discount<br>        Amount of Insurance Pay Portion<br>        Amount of Patient Pay Portion Disbursed to Provider<br>            through JC Cardholder Account<br>        Amount of Provider Discount<br>        Net Payment Amount |
| [TO BE DETERMINED] | Amount Denied Credit Referred back to Provider for Collection |
| MSF #48 | JCB Bills Patient for Patient Pay Portion |
| JCB → InsuredP | JCB sends a monthly statement to Insured, showing claim activity.<br>Information to include:<br>    JCB/Insured Account (Card) Number<br>    Insured's (CardHolder) Name<br>    Insured's (CardHolder) Address, Zip<br>    Date of Transaction<br>    Date of Service |

ADDENDUM-continued

SYSTEM INTERFACE DEFINITIONS
DETAIL INTERFACE DEFINITIONS

| | |
|---|---|
| | Line Item Description, to include:<br>    EOB/Claim Number<br>    Patient First Name<br>    Physician/Supplier Name (as much as will fit)<br>Patient Pay Dollar Amount<br>Payment since Last Statement<br>Minimum Payment<br>Terms of Payment<br>Balance Due<br>Payment Due Date |
| Concurrently:<br>MSF #21 | Insurance Company Produces EOB and Distributes to Provider & Patient |
| INS/TPA/SF → PRO/PATIENT<br>P<br>MSF #31 | INS/TPA/SF prepares EOB (Explanation of Benefits) and sends copies to Provider/Payee and Patient.<br>INS Forwards EOB Data to JC |
| INS/TPA/SF → JC/JCA<br>INS/TPA/SF → JC (PHASE II-Download)<br>P | INS/TPA/SF is responsible for sending EOB data regarding transaction to JC.<br>EOB data may be sent at time of processing EOB as an additional copy to JC.<br>In PHASE II, information may be sent as a daily download.<br>EOB Information to Include:<br>    Date of Transaction (ACH Date)<br>    Date of Service<br>    Group Policy Number<br>    Provider/Payee Name<br>    Provider/Payee Tax ID<br>    Insured Name<br>    Insured's Certificate Number<br>    Patient Name<br>    Patient Social Security (if available)<br>    EOB/Claim Number<br>    Billed Charges Amount<br>    Appropriate Discounts<br>    Exclusions: COB, etc.<br>    Insurance Pay Portion<br>    Patient Pay Portion<br>    Non Covered Charges |
| STEP 5d | VALIDATION OF PATIENT CREDIT LIMIT AND CREDIT RATING BY JCB;<br><br>SUBSEQUENT PAYMENT PROCESSING<br><br>Upon receipt of claim adjudication and reimbursement detail from INS/TPA/SF (MSF #25 for both Yes Credit and No Credit), JCB conducts an internal review and validation of Patient Pay Portion prior to the advancement of funds to Provider/Payee. JCB's review process validates Patient's Account based on two criteria:<br>    1) Has the Patient exceeded the Credit Limit imposed by JCB; and<br>    2) Has the Patient lapsed into a "No Credit" rating.<br>If both tests are negative, JCB proceeds with the next step described in MSF #26, STEPS 5, 5b and 5c.<br>If either of these tests are affirmative, JCB will post the Patient Pay portion onto a JCB Credit Exception List. JCB has the option to evaluate any Patient appearing on the Credit Exception List and to extend credit to them in the normal fashion. (See Continuation after MSF #26, STEPS 5, 5b and 5c).<br>JCB may also elect to report "no credit" and "credit exceptions" to JustCare, rather than to extend credit to a patient where their credit limits have been exceeded or where the patient has become delinquent since the original authorization was given. |
| MSF #53 | JCB Forwards "No Credit" Patient Data to JC |
| JCB → JC<br>P/E | JCB verifies credit status on all Insureds prior to making daily funds transfer (MSF #26). JC is notified of any patient pay transaction that cannot be transferred because of "no credit" on the day following identification. JCB faxes to JC information from the Post Adjudication Claim Record, to include:<br>    JCA ID<br>    Insured's Name<br>    Insured's Cert/Subscriber Number<br>    Patient's Name<br>    Patient Social Security<br>    Date of Service<br>    Physician/Supplier Name<br>    Provider/Payee Name,<br>    Provider/Payee I.D.<br>    EOB/Claim Number<br>    Patient Pay Amount<br>PHASE II NOTE: When JCB is capable of downloading "No Credit" Patient |

ADDENDUM-continued

SYSTEM INTERFACE DEFINITIONS
DETAIL INTERFACE DEFINITIONS

|   |   |
|---|---|
| | informtion, it is recommended that JCB download the entire "Post Adjudication Claim" Record. |
| | In Phase I JustCare will receive faxed information and notifies Provider/Payee for Balance Billing to Insured. After a single billing, the Provider/Payee has option to assign collection duties to JC. If authorization to collect patient pay amounts has been given to JC by Provider and, if circumstances warrant, JC combines the above listed information with the Insured's Data File and submits to the JC Collection Agency for collection proceedings. |
| | JC Collection Agency proceeds with precollect and collection efforts. If and when collected, JC Collection Agency notifies JC and deposits funds into JC Account. During Phase I period, JC will transfer monies collected by JC Collection Agency to Provider/Payee by Check. |
| | * * * * * * |
| NOTE: JCB TO DETERMINE THE FEASIBILITY OF THE FOLLOWING TWO MSF INTERACES, #54 AND 55, AT A LATER TIME: | |
| | 6) Date and Amount of Debit to JC Reserve Account with detail to include Insured's Name and Provider/Payee Name and Amount. |
| C. | JC receives JCB data regarding Bad Debt accounts and enters into JC Reserve Accounting System. |
| |    1) JC prepares and forwards Notice to Provider/Payees with Demand Statement for bad debts incurred by Insureds reported by JCB and judged by JC as "having the ability to pay" and those categorized as "disputed claims." Notice includes offer to Provider/Payee to assign Bad Debt back to JC for legal collection. |
| |    2) JC creates a follow-up method for return of funds and Assignment Statement from Provider/Payee. |
| |       (a) JC Posts funds received from Provider/Payee to JC Reserve |
| |       (b) JC forwards Bad Debt Assignments to JC Collection Agency |
| |          (1) Funds collected by JC Collection Agency are reported to JC and deposited with JC. |
| |          (2) JustCare sends check for funds collected to JCB to replenish JC Reserve. |
| |    3) JC identifies "can't pay" Bad Debt Accounts and analyzes for proper action, to include: |
| |       (a) Write off by JC Board of Directors |
| |       (b) Collection efforts by JC Collection Agency |
| |          (i) Amounts collected by JC Collection Aency are reported to and Deposited with JC |
| |          (ii) Deposited amounts transferred by JC to JC Reserve |
| |          (iii) Payment arrangements or judgement activity (liens, garnishments, etc) arranged by JC Collection Agency are maintained by JC Collection Agency and payments forwarded to JC as they become available. |
| | MONTHLY (OR AS DETERMINED) REPORTING ACTIVITY BY JCB FOR STEPS 5, 5b AND 5c: |
| | JCB is responsible to provide summary information on all insurance funding requests and the detail of all provider fund transfers to JC on a periodic basis. These steps are in a state of revision and only outline information is available. |
| MSF #28 | I. Provider/Payee Account Activity Statement |
| JCB → PRO (PHASE I-Hardcopy) | |
| JCB → PRO (PHASE II-May be downloaded to some Providers) | |
| P | Account Activity Statement has been replaced by the Enhanced Funds Transfer Notification (See MSF #26 and 27) to the Provider. |
| MSF #29 | II. Insurance Company Account Activity Statement |
| JCB → INS/TPA/SF (PHASE I-Hard Copy) | |
| JCB → INS/TPA/SF (PHASE II-Download) | |
| P | MSF #29 is in the process of being eliminated and replaced by a Confirmation for INS funding request by facsimile (fax) followed by a mailed notification of the same or enhanced information. Details are not presently available. (12/1/94) |
| MSF #30 | III. JCB Claims Summary Account Statement with JC Reserve Breakout |
| JCB → JC (PHASE I) | |
| JCB → JC (PHASE II-Download) | |
| P | |
| PART A | JCB is responsible to provide periodic downloads to JustCare of all information captured at the time of provider funds transfer. See MSF #26 and 27. Data elements to be included are: |
| |     Date of Transaction |
| |     Date of Service |
| |     Provider/Payee JCA ID |
| |     Insureds JCA ID |
| |     Policyholder Group Number |

ADDENDUM-continued

SYSTEM INTERFACE DEFINITIONS
DETAIL INTERFACE DEFINITIONS

|  |  |
|---|---|
|  | EOB/Claim Number |
|  | Insured's Name |
|  | Insured's Certificate/Subscriber Number |
|  | Patient Name |
|  | Patient Social Security (if available) |
|  | Provider/Payee Name |
|  | Provider/Payee Tax ID |
|  | Physician/Supplier Name |
|  | Gross Amount of Each Transaction |
|  |     Amount of JustCare Discount |
|  |     Amount of Insurance Pay Portion |
|  |     Amount of Patient Pay Portion Disbursed to Provider |
|  |         through JC Cardholder Account |
|  |     Amount of Provider Discount |
|  | Net Payment Amount |
| [TO BE DETERMINED] | Amount Denied Credit - Referred back to Provider for Collection |
|  | JC is responsible for internal analysis reporting and disbursement of any INS/TPA/SF specific or global reporting to INS/TPA/SF. |
| PART B | JCB is Responsible to provide to JC a Statement of JC Reserve General Ledger Account activity. The form of this report has not been fully determined. |
| NOTE: | NOT INCLUDED IN THE PROVIDER ACTIVITY REPORTS IS THE INCLUSION OF THE PROVIDER DISCOUNT SUBTRACTED FROM THE PATIENT PAY PORTION. INCLUSION OF THE PROVIDER DISCOUNTS IN MONTHLY REPORTING WILL BE DETERMINED AT A LATER TIME. |
|  | MONTHLY (OR BY ARRANGEMENT) REPORTING ACTIVITY BY INS/TPA/SF (for STEPS 5, 5b and 5c): |
|  | INS/TPA/SF is responsible to provide reports of claim activity to JC, including Summary EOB Data and adjudication of Dollar Amounts. Reports are identified I.–III. below. (MSF #31, 32 and 33) |
| MSF #31 | I. Combined EOB and Electronic Paid Claims Report |
| INS/TPA/SF → JCA/JC<br>INS/TPA/SF → JC (PHASE II)<br>P/E* | INS/TPA/SF sends combined EOB and/or Paid Claims Report to JC/JCA.<br>Report to contain: |
|  |     Date of Transaction (ACH Date) |
|  |     Date of Service |
|  |     Group Policy Number |
|  |     Provider/Payee Name |
|  |     Provider/Payee Tax ID |
|  |     Insured Name |
|  |     Insured's Certificate Number |
|  |     Patient Name |
|  |     Patient Social Security (if available) |
|  |     EOB/Claim Number |
|  |     Billed Charges Amount |
|  |     Appropriate Discounts |
|  |     Exclusions: COB, etc. |
|  |     Insurance Pay Portion |
|  |     Patient Pay Portion |
|  |     Non Covered Charges |
| MSF #32 | II. Non-Participating Claims Data and Combined EOB Report |
| INS → JC/JCA<br>INS/TPA/SF → JC (PHASE II)<br>P/E* | INS sends Combined EOB and/or Paid Claims Report for Non-Participating Services to JC/JCA. Report to Contain: |
|  |     Date of Transaction (ACH Date) |
|  |     Date of Service |
|  |     Group Policy Number |
|  |     Provider/Payee Name |
|  |     Provider/Payee Tax ID |
|  |     Insured Name |
|  |     Insured's Certificate Number |
|  |     Patient Name |
|  |     Patient Social Security (if available) |
|  |     EOB/Claim Number |
|  |     Billed Charges Amount |
|  |     Appropriate Discounts |
|  |     Exclusions: COB, etc. |
|  |     Insurance Pay Portion |
|  |     Patient Pay Portion |
|  |     Non Covered Charges |
| MSF #33 | II. EOB Report of Patient Direct Paid Claims |
| INS/TPA/SF → JCA<br>INS/TPA/SF → JC (PHASE II)<br>P/E* | INS/TPA/SF sends Combined EOB and/or Paid Claims Report for Patient Direct Paid Claims. Report to include: |

ADDENDUM-continued

SYSTEM INTERFACE DEFINITIONS
DETAIL INTERFACE DEFINITIONS

Date of Transaction (ACH Date)
    Date of Service
    Group Policy Number
    Provider/Payee Name
    Provider/Payee Tax ID
    Insured Name
    Insured's Certificate Number
    Patient Name
    Patient Social Security (if available)
    EOB/Claim Number
    Billed Charges Amount
    Appropriate Discounts
    Exclusions: COB, etc.
    Insurance Pay Portion
    Patient Pay Portion
    Non Covered Charges

PERIODIC REPORTING ACTIVITY BY JCA: (PHASE I)

JCA is responsible to provide a utilization reporting process to JC and to PRO organizations (IPAs, PHOs, Hospitals, etc.) These reports will detail all claim activity and will include:
    Provider Organization Designation
    Provider/Payee Name/ID Code
    Physician/Supplier Name
    Provider Type Code
    JustCare Authorization Number
    Insured's Name
    Insured's Certificate/Subscriber Number
    Patient Name
    Patient Social Security Number (if Available)
    INS/TPA/SF Name
    Group Policy Number
    Date of Birth
    Sex of Employee
    Date of Service
    Location (Hospital, office, ER, ambulatory surgical center, etc.)
    Procedure Codes, Drug Codes, etc. with Description
    Diagnosis Code
        (to include a maximum of 3 ICD-9-CM codes if
        available from claim submission) and Description
    Billed Charges
    Repriced Charges

STEP 6

ON-GOING MAINTENANCE:

ENROLLMENT ADDITIONS, CHANGES AND DELETIONS

MSF #34

Additions, Changes, and Deletions for Purchasers, Insureds and Dependents

Purchaser → INS/TPA/SF
P

Purchaser may incur corporate changes that need to be forwarded to INS/TPA/SF.
Purchaser would report:
    Group Name (need in all circumstances for identification)
    Group Number (need in all circumstances for identification)
and provide the following types of changes:
    Purchaser Address changes
    Purchaser Phone Number changes
    Change of Bank information
As enrollment additions, changes and deletions occur, PUR forwards* to INS/TPA/SF appropriate change information to reflect:
    Enrollment Data and Effective Dates of New Employees
    Name and Effective Date of Terminated Employees
    Name Changes
    Address Changes
    Dependent Additions or Deletions
    Tier Rating Changes
    Employment Status Changes - rehire, reinstate, on leave, etc.
    COBRA Changes
* PUR may report changes to INS/TPA/SF by letter, through forms designed and made available by INS/TPA/SF, or uses an electronic download method.

MSF #35

Additions, Changes, and Deletions for Purchasers, Insureds and Dependents

INS/TPA/SF → JCB
E or P

PURCHASER CHANGES:
Purchaser Changes that affect the JCB Purchaser Record are reported to INS/TPA/SF will be downloaded to JCB by INS/TPA/SF, to include:

ADDENDUM-continued

SYSTEM INTERFACE DEFINITIONS
DETAIL INTERFACE DEFINITIONS

Purchaser Address
Purchaser Phone Number
Purchaser Changes that affect a Change of Bank Account Authorization information will require hard copy documentation and data entry by JCB.
As enrollment additions, changes and terminations are received by INS/TPA/SF, INS/TPA/SF processes enrollment changes and downloads to JCB a new insured's Record for each affected employee reflecting the addition, change or deletion.

NEW EMPLOYEES AND LATE ENROLLEES, TO INCLUDE:

| Field | Type | Length |
|---|---|---|
| Record Type | Numeric | (2) |
| JCA ID | Alpha | (8) |
| INS/TPA/SF ID | Alpha | (10) |
| Insured's Name (Primary Name) | Alpha | (25) |
| Primary BirthDate (MMDDYY) | Numeric | (6) |
| Dependents | Numeric | (2) |
| * Insured's First Line Address | Alpha | (30) |
| * Insured's Second Line Address | Alpha | (20) |
| * Insured's City, State ID | Alpha | (22) |
| * Insured's Zip | Numeric | (5) |
| * Insured's Zip Suffix | Numeric | (4) |
| * Insured's Home Phone Number | Numeric | (10) |

* INS/TPA/SF to obtain and transfer to JCB. In the event INS/TPA/SF is incapable of providing data elements (*'d) to JCB, JCB will obtain from Cardholder Agreement and enter into their system.

| Field | Type | Length |
|---|---|---|
| Insured's Social Security Number | Numeric | (9) |
| Insured's Cert/Subscriber Number | Alpha | (10) |
| Group Policy Number | Alpha | (10) |
| Additional Reference (i.e. subsidiary of purchaser, etc.) | Alpha | (40) |
| Cobra Reference | (Alpha) | (1) |
| Primary Care Provider ID | (Alpha) | (10) |
| CoApp (Spouse) Name | Alpha | (25) |
| CoApp (Spouse) SSN | Numeric | (9) |
| A/C   A = Add = Issue Card | Alpha | (1) |
| Maximum Out of Pocket | Numeric | (S9,2) |
| Tier Rating | Numeric | (1) |

1 = Employee Only
2 = Employee & Spouse
3 = Employee & Dependent(s)
4 = Full Family

| Field | Type | Length |
|---|---|---|
| Effective Date of Coverage | Numeric | Julian Date |
| Credit (Y/N) | Alpha | (1) |
| Eligible (Y/N) | Alpha | (1) |

INS/TPA/SF responsible for the completion and delivery of the following form to JC:
JustCare Individual Consumer Member Application and Agreement
INS/TPA/SF delivers to JustCare the JustCare Individual Consumer Member Application and Agreement. If necessary, INS Member approves or rejects insurance application. Individual Consumer Retains the second copy (pink).
JC receives from INS/TPA/SF the JustCare Individual Consumer Member Application and Agreement; JC separates the original (white) from the copy (yellow); batches and logs the originals (white) and retains the copy (yellow) for JustCare's records.
JCB receives original JustCare Individual Consumer Member Application and Agreement from JC and receives download of insured's data from INS/TPA/SF. JCB enters Insured/Individual Consumer Member into into JCB data base and assigns:
JCB/Insured Account (Card) Number.

\* \* \* \* \*

FOR TERMINATED EMPLOYEES:
INS/TPA/SF transmits Insured's Record noting an Eligible = N on a Change Record.
JCB receives above information into data base and overlays Insured's Record with the change. Change Indicated is Eligible = N. The transfer by INS/TPA/SF will be made on the effective date of termination. Once the overlay has been made, the insured is no longer eligible for coverage.

Note: COBRA RECIPIENTS WILL BE TREATED AS NEW EMPLOYEE AND WILL RECEIVE NEW JCB/INSURED ACCOUNT CARD AND NUMBER. PURCHASER WILL REPORT EMPLOYEE'S DATE OF TERMINATION AND WILL REPORT SEPARATELY THE EMPLOYEES ELECTION TO COBRA WHEN MADE.
Purchaser wiil be required to have COBRA applicant submit the following form:
JustCare Individual Consumer Member Application and Agreement

\* \* \* \* \*

FOR CHANGES INCURRED BY INSURED EMPLOYEES:
INS/TPA/SF transmits Insured's Record after making changes and converting A/C Record Code Value to "C" = Change. Record remains active with data changes replacing previous data.

ADDENDUM-continued

SYSTEM INTERFACE DEFINITIONS
DETAIL INTERFACE DEFINITIONS

| | |
|---|---|
| NOTE: | If JCB receives an Insured's Record where the A/C flag = C, changes to the following data elements would prompt JCB to reissue a JC Card (same account, same account number):<br>    Insured's Name<br>    Group Policy Number<br>    Certificate Number<br>    Tier Rating<br>    JCA Identifier<br>In addition to the above, the following events initiated by INS/TPA/SF would trigger the establishment of a new account, also requiring the issuance of new cards:<br>    Election of COBRA by terminated Employees or Dependents of<br>        Employee (the Insured)<br>    Employment changes by Employee from one JC Payor Member to<br>        another JC Payor Member<br>Lost Cards reported to JCB would initiate a manual process by JCB to replace the card and may require that a new account be established. |
| STEP 6b | ON GOING MAINTENANCE: PREMIUM UPDATES - PHASE II<br><br>Prior to funds transfer, INS/TPA sends monthly premium information to PUR, relating current enrollment and premium information. PUR responds to INS/TPA with any changes to enrollment. |
| MSF #36 | Premium Updates for Billing Purchaser |
| INS/TPA → JCB<br>E | INS/TPA receives enrollment updates from PUR and determines increases, decreases, etc. to overall premium structure. INS/TPA notifies JCB by download process. Information to include:<br>    Purchaser (Group) Number<br>    Purchaser (Group) Name<br>    Updated Monthly Premium for Group |
| STEP 7 | AUTOMATED PREMIUM COLLECTION BY JCB |
| NOTE: | STEP 7 AND 7b ARE PHASE II OPERATIONS TO BE APPROVED PRIOR TO IMPLEMENTATION |
| A. | Monthly Premium Collection<br>Having received the adjusted premium amount (or using the prior month's premium amount if no updates have occurred), INS mails to Purchaser notification of monthly premium.<br>JCB then debits the Purchaser' JCB Account for the designated monthly premium amount. |
| MSF #37 | JCB EFT's premium from Purchaser's Bank Account, or Purchaser sends check |
| PUR Bank → JCB | to INS for premium. |
| or<br>PUR → JNS<br>E/P | Premium billing or Notice of Intent to Transfer Premium Dollar amount sent to Purchaser by INS. On predetermined date JCB EFT's premium amount from Purchaser's bank account to JCB.<br>Sequence of notification and collection activity to be predetermined by INS/TPA/SF and JC |
| B. | Collection of Past Due Premiums and<br>Cancellation of Purchaser for Non-Payment of Premium |
| MSF #38 | If Insufficient Funds for Electronic Transfer, JCB Notifies INS |
| JCB → INS<br>E/P | Failure to transfer funds from PUR's bank account results in notice of insufficient funds. JCB notifies INS through JCB's most efficient means (i.e. paper, electronic, etc.)<br>(Note: See MSF #47 for more detail on account "Hold" status.) |
| MSF #39 | If Insufficient Funds, INS notifies Purchaser that 31 day grace period has |
| INS → PUR | commenced. (Grace Period starts from premium due date.) |
| P | After receiving notice from JCB that PUR's account produced insufficient funds, INS sends paper document notice to PUR by overnight mail giving notice of insufficient funds and alerting PUR that 31 day grace period has begun. |
| MSF #40 | JCB EFT's Premium from JCB Insurance Company Account to INS bank account |
| JCB → INS<br>E | JCB EFT's premium collected since last transfer (daily) to INS Co. Bank Account, itemized by Group Number and accompanied by an information transmittal document. |
| MSF #47 | INS Notifies JCB to Cancel All JC Cards for Canceled Group |
| INS → JCB<br>E | If no payment is forthcoming after 31 day Grace Period, INS notifies JCB to cancel all JustCare Cards for Canceled Group. |

ADDENDUM-continued

SYSTEM INTERFACE DEFINITIONS
DETAIL INTERFACE DEFINITIONS

| | |
|---|---|
| C. | Treatment of Claims during Premium Past Due Collection Period |
| MSF #41 | Upon Expiration of 31 Day Grace Period, INS returns Claims Held to PRO |
| INS → PRO<br>P | Any PRO claims received during the 31 day grace period are held by INS until determination of premium payment. If no payment received, any claims held will be returned to PRO, marked "No Coverage, No Credit." |
| MSF #41b | Upon Expiration of 31 Day Grace Period, INS Forwards Unpaid EOB to Insured |
| INS → JC<br>P | Any PRO claims received during the 31 day grace period are held by INS until determination of premium payment. If no payment received, INS forwards copy of Unpaid EOB to Insured. |
| MSF #41c | Upon Expiration of 31 Day Grace Period, INS Notifies JC of Claims Returned |
| INS → JC<br>P | Any PRO claims received during the 31 day grace period are held by INS until determination of premium payment. If no payment received, INS forwards copy of Unpaid EOB to JC. |
| D. | Monthly Premium Reporting Activity by JCB |
| MSF #42 | Premium Account Activity Statement to INS |
| JCB → INS<br>P | JCB provides monthly statement showing account activity of all premium notices from INS and all Premium transfers made. Statement to include:<br>    Statement Date<br>        By group, the following premium information:<br>            Beginning Balance (Premium Paid since last Statement)<br>                Total Premium Notices received from INS during month<br>                Total Premium Transfers made from PUR to JCB<br>                Total Premium Transfers made from JCB to INS<br>            Ending Balance (Showing Premium Paid to Date at End of Month |
| MSF #43 | Premium Account Activity Statement to JC |
| JCB → JC<br>P | JCB provides monthly statement showing account activity of all premium notices collected from all INS and all Premium transfers made.<br>Statement to include:<br>    Statement Date<br>    INS Name<br>    Group Name<br>    Group Policy Number<br>    Beginning Balance by Group Name and Number<br>        (Premium Paid since last Statement)<br>    Total Premium Notices received from INS during month<br>    Total Premium Transfers made from PUR to JCB<br>    Total Premium Transfers made from JCB to INS<br>    Ending Balance for each Group<br>        (Premium Paid to Date at End of Month)<br>    Total Premiums Collected at End of Month for each INS |
| STEP 7b | PREMIUM COLLECTION FOR DIRECT PAYMENT TO INS |
| A. | Monthly Premium Collection by INS<br>Where INS chooses or is incapable of receiving automatic premium collection or where PUR elects not to authorize automatic premium payments, the notification of monthly premium will be considered an invoice, payable in 30 days, and PUR will pay invoice manually by check or money order. |
| B. | Collection of Past Due Premiums to INS and<br>Cancellation of Purchaser for Nonpayment of Premium<br>If PUR fails to make payment of monthly premium to INS on a timely basis, INS will notify Purchaser that a 31-day grace period has commenced. Patient then has an additional 31 days to make payment of premium.<br>If payment is not received during the 31-day grace period, INS notifies JCB that all JC cards are canceled for the group. |
| MSF #47 | INS Notifies JCB to Cancel All JC Cards for Canceled Group |
| INS → JCB<br>E | If no payment is forthcoming after 31 day Grace Perfod, INS notifies JCB to cancel all JustCare Cards for Canceled Group.<br>Note: If JCB agrees, JCB can put entire account on hold status for 30 days for possible reinstatement. JC/Insured Account Cards would also be placed on a "Hold" status. Use of the card would then generate a "no coverage, no credit" response when used by a Provider to verify eligibility.<br>When the JustCare Cards are canceled, INS must notify the Purchaser that all coverage has been canceled. Purchaser must then notify Insured that coverage has ceased and that JustCare cards are no longer activated. INS must also notify JC of Notice of Cancellation.<br>If Purchaser remits monthly premium past the 31-day grace period, the Group Policy may be reinstated by INS, in which case this information also would be provided to JC. |

ADDENDUM-continued

SYSTEM INTERFACE DEFINITIONS
DETAIL INTERFACE DEFINITIONS

| | |
|---|---|
| C. | Treatment of Claims during Premium Past Due Collection Period |
| MSF #41 | Upon Expiration of 31 Day Grace Period, INS returns Claims Held to PRO |
| INS → PRO<br>P | Any PRO claims received during the 31 day grace period are held by INS until determination of premium payment. If no payment received, any claims held will be returned to PRO, marked "No Coverage, No Credit." |
| MSF #41b | Upon Expiration of 31 Day Grace Period, INS Forwards Unpaid EOB to Insured |
| INS → JC<br>P | Any PRO claims received during the 31 day grace period are held by INS until determination of premium payment. If no payment received, INS forwards copy of Unpaid EOB to insured. |
| MSF #41c | Upon Expiration of 31 Day Grace Period, INS Notifies JC of Claims Returned |
| INS → JC<br>P | Any PRO claims received during the 31 day grace period are held by INS until determination of premium payment. If no payment received, INS forwards copy of Unpaid EOB to JC. |
| D. | Monthly Premium Reporting Activity by INS |
| MSF #46 | Premium Collected Report |
| INS → JC<br>P | INS provides to JC a monthly report of Total Premiums Collected directly from Purchaser (checks or money orders). Report to include:<br>    Statement Date<br>    Date of Receipt of Payments<br>    Amount Received by Group Number<br>    Number of Employees |

APPENDIX
SEQUENCE OF ACTIVITY REGARDING JUSTCARE TRANSACTIONAL FEES

The sequence of activity regarding the JustCare transactional Administrative Fee and the Provider Discount is as follows:

| | |
|---|---|
| MSF #23 | JCA adds transactional administrative fee to priced claim. |
| | Transactional Administrative Fee is added to and becomes a part of the priced claim by JCA. |
| INS/TPA/SF receives and adjudicates claim, inclusive of any transactional administrative fee. | |
| MSF #24 & 25 | INS/TPA/SF transmits Post Adjudication claim data, broken out into INS/TPA/SF Pay Portion and Patient Pay Portion, to the JCB. |
| MSF #26 | (Patient Pay Portion)<br><br>JCB debits the credit card account<br>JCB credits Internal JCB/Credit Card Account<br>JCB debits the Internal JCB/Credit Card Account<br>JCB credits the JC Account the transactional administrative fee<br>JCB credits balance to the Provider Account,<br>    less Provider Discount (Merchant Fee)<br>JCB transfers balance by electronic deposit to Provider Bank<br>    Account |
| MSF #27 | (Insurance Pay Portion)<br><br>JCB debits the Payor Account *INS/TPA/SF by ACH transfer<br>JCB credits an Internal JCB/Payor Account<br>JCB debits the Internal JCB/Payor Account<br>JCB credits the JC Account the transactional administrative fee<br>JCB credits balance to the Provider Account<br>JCB transfers balance by electronic deposit to Provider Bank<br>    Account<br>JCB debits the Internal JCB/Payor and Credit Card Account<br>JCB credits   1) the JC Account (administrative Transactional Fee)<br>                2) the JCB Provider Account |

JCB faxes/mails daily confirmation notice of transactional administrative fee detail with monthly summary reporting.

KEY:
JC: JustCare
PRO: Provider/Payee
E: Electronic
P: Paper
JCA: JustCare Administrator
JCB: JustCare Bank
PUR: Purchaser
C: Card

ADDENDUM-continued

SYSTEM INTERFACE DEFINITIONS
DETAIL INTERFACE DEFINITIONS

TPA/SF: Third Party Administrator/Self Funded
ECP: Electronic Claims Processor
INS: Insurance Co.
800: 800 Phone No.
T: Telephone

What is claimed is:

1. A method for effectuating a cooperative health care provision and management agency system through a data switch and repository device, said method comprising the steps of:

configuring said agency system to serve only a plurality of entities who have mutually agreed to participate in said agency system by way of a plurality of interdependent agency agreements executed by said plurality of entities;

said plurality of entities including health care providers, at least one financial institution, at least one insurance organization, a management service having said data switch and repository device, purchasing members who have one or more health care users as members, and health care users who qualify as an insurance organization via self insurance;

said mutual agreement to participate in said agency system by way of said plurality of interdependent agency agreements including authority mutually granted by said plurality of entities to said at least one insurance organization to adjudicate claims that are transmitted by said health care providers to said at least one insurance organization;

providing for said data switch and repository device to communicate data transmission among said plurality of entities and to record transactions between said plurality of entities;

compiling an entity list at said data switch and repository device, said entity list listing said plurality of entities;

updating said entity list as changes in a status of any of said plurality of entities occur;

electronically transmitting an inquiry from a given health care provider to said data switch and repository device relative to a given user;

electronically responding to said inquiry by transmitting a verification from said data switch and repository device to said given health care provider that said given user is eligible to receive care as an entity of said agency system;

electronically transmitting a claim from said given health care provider to said at least one insurance organization, said claim including codes indicating a diagnosis and treatment provided to said given user;

adjudicating at said at least one insurance organization said transmitted claim, and electronically notifying said given health care provider of the results of said adjudication;

responding to a favorable result of said adjudicating step by electronically transmitting a direction from said at least one insurance organization to a financial institution, said transmission authorizing said financial institution to pay said claim to the extent that said at least one insurance organization has adjudicated that said claim is payable; and electronically transmitting from said at least one insurance organization to said given health care provider an explanation of benefits as determined from said adjudication.

2. The method of claim 1 including the steps of:

issuing to all of said users an electronic card that is usable only in said agency system for enabling automatic communication by said purchasing members through said data switch and repository device; and using said data switch and repository device to provide reports of transactions between said plurality of entities for analyzing financial interchanges between said plurality of entities.

3. The method of claim 2 including the steps of:

determining an amount of credit extendible to said given user;

establishing an amount of said claim that is appropriate but in excess of an amount authorized for payment by said adjudicating step; and authorizing payment in an amount in conformity with said determining step and said establishing step.

4. The method of claim 3 including the step of:

collecting information concerning health care provider performance from transmissions through said data switch and repository device.

* * * * *